United States Patent [19]
Andersen et al.

[11] Patent Number: 6,043,247
[45] Date of Patent: Mar. 28, 2000

[54] MODULATORS OF MOLECULES WITH PHOSPHOTYROSINE RECOGNITION UNITS

[75] Inventors: Henrik Sune Andersen; Niels Peter Hundahl Møller, both of København; Peter Madsen, Bagsværd, all of Denmark

[73] Assignee: Novo Nordisk A/S, Bagsværd, Denmark

[21] Appl. No.: 08/842,800

[22] Filed: Apr. 16, 1997

Related U.S. Application Data

[60] Provisional application No. 60/023,661, Jul. 17, 1996.

[30] Foreign Application Priority Data

Apr. 19, 1996 [DK] Denmark .................................. 0463/96
Dec. 17, 1996 [DK] Denmark .................................. 1436/96

[51] Int. Cl.$^{7}$ .......................... A01N 43/54; A01N 37/10; C07C 69/76; C07C 229/00
[52] U.S. Cl. .......................... 514/255; 514/517; 514/532; 514/534; 514/535; 514/539; 544/363; 544/382; 544/392; 560/8; 560/11; 560/12; 560/19; 560/27; 560/48; 560/55; 560/57; 560/59; 560/101; 560/102; 562/433; 562/441; 562/491
[58] Field of Search .......................... 549/445; 544/363, 544/382, 392; 560/8, 11, 12, 19, 27, 48, 55, 57, 59, 101; 562/433, 441, 491; 514/866, 755, 517, 532, 534, 535, 539

[56] References Cited

U.S. PATENT DOCUMENTS 5,770,620  6/1998  Mijalli et al. .......................... 548/495

FOREIGN PATENT DOCUMENTS 23 16 881    10/1973   Germany.
25 17 229    10/1976   Germany.
2 205 240    12/1988   United Kingdom.
WO 93/21783  11/1993   WIPO.
WO 97/08934   3/1997   WIPO.

OTHER PUBLICATIONS

Williamson et al, Chem. Abstract vol. 78 No. 97492, "Heterocyclic Antiinflammatory Agents", 1972.
El–Batouti, Chem. Abstract vol. 123 No. 293698, "Cinnamic acid der. as inhibitors for dissolution of copper in phosphoric acid." 1995.
Lohaus et al, Chem. abstract, vol. 66 No. 75634. "Friedel–Crafts react. of β dialkylacrylic acid esters."1967.
Blank, et al., Journal of Medicinal Chemistry, vol. 22, No. 7, pp. 840–844, (1979).
Sugihara et al., Arzneim.–Forsch (Drug Res.), vol. 24, No. 10, pp. 1560–1563 (1974).
Cao et al., Bioorganic & Medicinal Chemistry Letters, vol. 5, No. 24, pp. 2953–2958 (1995).
Moran et al., J. Am. Chem. Soc., vol. 117, pp. 10787–10788 (1995).

*Primary Examiner*—John Kight
*Assistant Examiner*—Raymond Covington
*Attorney, Agent, or Firm*—Steve T. Zelson, Esq.; Elias Lambiris, Esq.

[57] ABSTRACT

The present invention relates to novel substituted acrylic acids, to methods for their preparation, compositions containing them, and their use for treatment of human and animal disorders, to their use for purification of proteins or glycoproteins, and to their use in diagnosis. The invention also relates to modulation of the activity of molecules with phospho-tyrosine recognition units, including protein tyrosine phosphatases (PTPases) and proteins with Src-homology-2 domains, in in vitro systems, microorganisms, eukaryotic cells, whole animals and human beings.

35 Claims, No Drawings

```
                          SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 7 amino acids
         (B) TYPE: amino acid
         (C) STRANDEDNESS: single
         (D) TOPOLOGY: linear (xi) SEQUENCE DESCRIPTION: SEQ ID NO:1:

Cys Xaa Xaa Xaa Xaa Xaa Arg
  1               5

(2) INFORMATION FOR SEQ ID NO:2:

(i) SEQUENCE CHARACTERISTICS:
         (A) LENGTH: 8 amino acids
         (B) TYPE: amino acid
         (C) STRANDEDNESS: single
         (D) TOPOLOGY: linear (xi) SEQUENCE DESCRIPTION: SEQ ID NO:2:

His Cys Xaa Xaa Gly Xaa Xaa Arg
  1               5

(2) INFORMATION FOR SEQ ID NO:3:

(i) SEQUENCE CHARACTERISTICS:
         (A) LENGTH: 12 amino acids
         (B) TYPE: amino acid
         (C) STRANDEDNESS: single
         (D) TOPOLOGY: linear (xi) SEQUENCE DESCRIPTION: SEQ ID NO:3:

Thr Arg Asp Ile Xaa Glu Thr Asp Xaa Xaa Arg Lys
  1               5                  10

(2) INFORMATION FOR SEQ ID NO:4:

(i) SEQUENCE CHARACTERISTICS:
         (A) LENGTH: 4 amino acids
         (B) TYPE: amino acid
         (C) STRANDEDNESS: single
         (D) TOPOLOGY: linear (xi) SEQUENCE DESCRIPTION: SEQ ID NO:4:

Tyr Glu Glu Ile
```

MODULATORS OF MOLECULES WITH PHOSPHOTYROSINE RECOGNITION UNITS

CROSS-REFERENCE TO RELATED APPLICATIONS

This application claims priority under 35 U.S.C. 119 of U.S. provisional application Ser. No. 60/023,661 filed on Jul. 17, 1996 and Danish application Ser. Nos. 0463/96 filed Apr. 19, 1996 and 1436/96 filed Dec. 17, 1996, the contents of which are fully incorporated herein by reference.

FIELD OF THE INVENTION

The present invention relates to novel substituted acrylic acids, to methods for their preparation, to compositions containing them, to their use for treatment of human and animal disorders, to their use for purification of proteins or glycoproteins, and to their use in diagnosis. The invention relates to modulation of the activity of molecules with phospho-tyrosine recognition units, including protein tyrosine phosphatases (PTPases) and proteins with Src-homology-2 domains, in in vitro systems, microorganisms, eukaryotic cells, whole animals and human beings.

BACKGROUND OF THE INVENTION

Phosphorylation of proteins is a fundamental mechanism for regulation of many cellular processes. Although protein phosphorylation at serine and threonine residues is quantitatively dominating in eukaryotic cells, reversible tyrosine phosphorylation seems to play a pivotal role in regulation of cell growth and differentiation as well as in neoplastic transformation (Hunter, *Cell* 80: 225–236 (1995); Schlessinger and Ullrich, *Neuron* 9: 383–391 (1992); Cantley et al., *Cell* 64: 281–302 (1991); Ullrich and Schlessinger, *Cell* 61:203–212(1990); Hunter, *Curr. Opin. Cell. Biol.* 1:1168–1181 (1989)); Hunter and Cooper, *Annu. Rev. Biochem.* 54: 897–930 (1985)).

The regulation of protein tyrosine phosphorylation in vivo is mediated by the opposing actions of protein tyrosine kinases (PTKs) and protein tyrosine phosphatases (PTPases). The level of protein tyrosine phosphorylation of cellular proteins is determined by the balanced activities of PTKs and PTPase (Hunter, 1995, supra).

PTPases—an overview

The protein phosphatases are composed of at least two separate and distinct families (Hunter, T., *Cell* 58: 1013–1016 (1989)) the protein serine/threonine phosphatases and PTPases.

The PTPases are a family of enzymes that can be classified into two groups: a) intracellular or nontransmembrane PTPases and b) receptor-type or transmembrane PTPases.

Intracellular PTPases: All known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. *TIBS* 19: 151–155 (1994)). The first intracellular PTPase to be purified and characterized was PTP1B which was isolated from human placenta (Tonks et al., *J. Biol. Chem.* 263: 6722–6730 (1988)). Shortly after, PTP1B was cloned (Charbonneau et al., *Proc. Natl. Acad. Sci. U.S.A.* 86: 5252–5256 (1989); Chernoff et al., *Proc. Natl. Acad. Sci. U.S.A.* 87: 2735–2789 (1989)). Other examples of intracellular PTPases include (1) T-cell PTPase (Cool et al. *Proc. Natl. Acad. Sci. U.S.A.* 86: 5257–5261 (1989)), (2) rat brain PTPase (Guan et al., *Proc. Natl. Acad. Sci. U.S.A.* 87:1501–1502 (1990)), (3) neuronal phosphatase STEP (Lombroso et al., *Proc. Natl. Acad. Sci. U.S.A.* 88: 7242–7246 (1991)), (4) ezrin-domain containing PTPases: PTPMEG1 (Guet al., *Proc. Natl. Acad. Sci. U.S.A.* 88: 5867–57871 (1991)), PTPH1 Yang and Tonks, *Proc. Natl. Acad. Sci. U.S.A.* 88: 5949–5953 (1991), PTPD1 and PTPD2 (Møller et al., *Proc. Natl. Acad. Sci. U.S.A.* 91: 7477–7481 (1994)), FAP-1/BAS (Sato et al., *Science* 268: 411–415 (1995); Banville et al., *J. Biol. Chem.* 269: 22320–22327 (1994); Maekawa et al., *FEBS Letter* 337: 200–206 (1994)), and SH2 domain containing PTPases: PTP1C/SH-PTP1 (Plutzky et al., *Proc. Natl. Acad. Sci. U.S.A.* 89:1123–1127 (1992); Shen et al., *Nature Lond.* 352:736–739 (1991)) and PTP1D/Syp/SH-PTP2 (Vogel et al., *Science* 259: 1611–1614 (1993); Feng et al., *Science* 259:1607–1611(1993); Bastein et al., *Biochem. Biophys. Res. Comm.* 196: 124–133 (1993)).

Low molecular weight phosphotyrosine-protein phosphatase (LMW-PTPase) shows very little sequence identity to the intracellular PTPases described above. However, this enzyme belongs to the PTPase family due to the following characteristics: (i) it possesses the PTPase active site motif: Cys-Xxx-Xxx-Xxx-Xxx-Xxx-Arg (SEQ ID NO:1) (Cirri et al., *Eur. J. Biochem.* 214: 647–657 (1993)); (ii) this Cys residue forms a phospho-intermediate during the catalytic reaction similar to the situation with 'classical' PTPases (Cirri et al, supra; Chiarugi et al., *FEBS Lett.* 310: 9–12 (1992)); (iii) the overall folding of the molecule shows a surprising degree of similarity to that of PTP1B and Yersinia PTP (Su et al., *Nature* 370: 575–578 (1994)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45ILCA (Ralph, S. J., *EMBO J.* 6:1251–1257 (1987)) and (2) LAR (Streuli et al., *J. Exp. Med.* 168: 1523–1530 (1988)) that were recognized to belong to this class of enzymes based on homology to PTP1B (Charbonneau et al., *Proc. Natl. Acad. Sci. U.S.A.* 86: 5252–5256 (1989)). CD45 is a family of high molecular weight glycoproteins and is one of the most abundant leukocyte cell surface glycoproteins and appears to be exclusively expressed upon cells of the hematopoietic system (Trowbridge and Thomas, *Ann. Rev. Immunol.* 12: 85–116 (1994)).

The identification of CD45 and LAR as members of the PTPase family was quickly followed by identification and cloning of several different members of the receptor-type PTPase group. Thus, 5 different PTPases, (3) PTPα, (4) PTPβ, (5) PTPδ, (6) PTPε, and (7) PTPζ, were identified in one early study (Krueger et al., *EMBO J.* 9: 3241–3252 (1990)). Other examples of receptor-type PTPases include (8) PTPγ (Barnea et al., *Mol. Cell. Biol.* 13:1497–1506 (1995)) which, like PTPζ (Krueger and Saito, *Proc. Natl. Acad. Sci. U.S.A.* 89: 7417–7421 (1992)) contains a carbonic anhydrase-like domain in the extracellular region, (9) PTPμ (Gebbink et al., *FEBS Letters* 290: 123–130 (1991), (10) PTPκ (Jiang et al., *Mol. Cell. Biol.* 13:2942–2951 (1993)). Based on structural differences the receptor-type PTPases may be classified into subtypes (Fischer et al., *Science* 253: 401–406 (1991)): (I) CD45; (II) LAR, PTPδ, (11) PTPσ; (III) PTPβ, (12) SAP-1 (Matozaki et al., *J. Biol. Chem.* 269: 2075–2081 (1994)), (13) PTP-U2/GLEPP1 (Seimiya et al., Oncogene 10: 1731–1738 (1995); (Thomas et al., *J. Biol. Chem.* 269:19953–19962 (1994)), and (14) DEP-1; (IV) PTPα, PTPε. All receptor-type PTPases except Type IV contain two PTPase domains. Novel PTPases are continously identified, and it is anticipated that more than 500 different species will be found in the human genome, i.e. close to the predicted size of the protein tyrosine kinase superfamily (Hanks and Hunter, *FASEB J.* 9: 576–596 (1995)).

PTPases are the biological counterparts to protein tyrosine kinases (PTKs). Therefore, one important function of PTPases is to control, down-regulate, the activity of PTKs. However, a more complex picture of the function of PTPases now emerges. Several studies have shown that some PTPases may actually act as positive mediators of cellular signaling. As an example, the SH2 domain-containing PTP1D seems to act as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous PTP1 C seems to act as a negative regulator of growth factor-stimulated proliferation (Bignon and Siminovitch, *Clin. Immunol. Immunopathol.* 73:168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, possibly through dephosphorylation of the C-terminal tyrosine of Fyn and Lck (Chan et al., *Annu. Rev. Immunol.* 12: 555–592 (1994)).

Dual specificity protein tyrosine phosphatases (dsPTPases) define a subclass within the PTPases family that can hydrolyze phosphate from phosphortyrosine as well as from phosphor-serine/threonine. dsPTPases contain the signature sequence of PTPases: His-Cys-Xxx-Xxx-Gly-Xxx-Xxx-Arg (SEQ ID NO:2). At least three dsPTPases have been shown to dephosphorylate and inactivate extracellular signal-regulated kinase (ERKs)/mitogen-activated protein kinase (MAPK): MAPK phosphatase (CL100, 3CH134) (Charles et al., *Proc. Natl. Acad. Sci. U.S.A.* 90: 5292–5296 (1993)); PAC-1 (Ward et al., *Nature* 367: 651–654 (1994)); rVH6 (Mourey et al., *J. Biol. Chem.* 271: 3795–3802 (1996)). Transcription of dsPTPases are induced by different stimuli, e.g. oxidative stress or heat shock (Ishibashi et al., *J. Biol. Chem.* 269: 29897–29902 (1994); Keyse and Emslie, *Nature* 359: 644–647 (1992)). Further, they may be involved in regulation of the cell cycle: cdc25 (Millar and Russell, *Cell* 68: 407–410 (1992)); KAP (Hannon et al., *Proc. Natl. Acad. Sci. U.S.A.* 91: 1731–1735 (1994)). Interestingly, tyrosine dephosphorylation of cdc2 by a dual specific phosphatase, cdc25, is required for induction of mitosis in yeast (review by Walton and Dixon, *Annu. Rev. Biochem.* 62: 101–120 (1993)).

PTPase specificity

Several studies have addressed the question of PTPase specificity using synthetic peptides and provided important insight with respect to primary structural sequence requirements for substrate recognition (Ramachandran et al., *Biochemistry* 31: 4232–4238 (1992); Cho, H. et al., *Biochemistry* 31: 133–138 (1992); Zhang, Z-Y. et al., *Proc. Natl. Acad. Sci. U.S.A.* 90, 4446–4450 (1993); Zhang, Z.-Y. et al., *Biochemistry* 33: 2285–2290 (1994)). However, an obvious limitation of this approach is the lack of defined three-dimensional structure of the peptide analogs. Likewise, the PTPases utilized for these analyses are removed from their natural environment. Since at least part of the PTPase specificity seems to be conveyed by a defined subcellular localization (Mauro and Dixon, *TIBS* 19: 151–155 (1994)), it is essential that such studies are complemented with measurements of PTPase activity towards cellular substrates in intact cells.

Phosphotyrosine recognition in signal transduction

Hormones, growth factors, cytokines, antigens, extracellular matrix components as well as molecules positioned at the cell surface induce signal transduction by binding to specific cell surface structures or receptors on target cells (reviewed in Pawson, *Nature* 373: 573–580 (1995)). The resulting cellular signal is often mediated through a series of phosphorylation and dephosphorylation reactions on tyrosine residues of signaling molecules. To allow efficient and selective signaling, several recognition units for phosphotyrosine (pTyr) have developed during evolution: a) PTPases; b) Src-homology-2 (SH2) domains; c) pTyr-binding (PTB) domains. As described above, the recognition of pTyr by PTPases leads to dephosphorylation with concommitant dissociation from the molecular target. Dephosphorylation may either lead to upregulation or downregulation of the signal. In contrast, SH2 domains and PTB domains primarily act as docking molecules with little or no catalytic activity. In other words, tyrosine phosphorylated proteins have the capacity to bind other proteins containing SH2 domains or PTB domains thereby controlling the subcellular location of signaling molecules. There appears to be a significant degree of selectivity in SH2 domain recognition of pTyr and their surroundings. Thus, SH2 domains from the Src kinase family bind the peptide pTyr-Glu-Glu-Ile (SEQ ID NO:4) in a relatively selective manner, whereas the PTPD1 seems to recognize at least five, primarily hydrophobic residues C-terminal to the pTyr (Pawson, supra). Certain PTPase domains, in particular the C-terminal domain of some receptor-type PTPases, seem to have little or no catalytic activity. It may be hypothesized that these domains have a function as pTyr recognition units similar to SH2 domains and PTB domains. Inhibition of signal transduction processes could, in principle, be achieved by using non-hydrolyzable pTyr-containing peptides with preferential affinity for specific PTPases, SH2 domains or PTB domains. However, due to the lack of efficient bioavailability of peptides there is a need for development of either peptidomimetics or novel small molecules with preferential binding to pTyr recognition units of specific cellular targets. Such selective compounds can either initiate, increase or decrease defined signal transduction processes.

PTPases: Inhibitors

In an early study, vanadate was found to inhibit protein-tyrosine phosphatases in mammalian cells with a concomitant increase in the level of phosphotyrosine in cellular proteins leading to transformation (Klarlund, *Cell* 41: 707–717 (1985)). Vanadium-based phosphatase inhibitors are relatively unspecific. Therefore, to assess the importance of specific structures on PTPase activity more selective inhibitors are needed. One possibility for obtaining selective PTPase inhibitors would be through design of different ancillary ligands for peroxovanadium-based compounds (Posner et al., *J. Biol. Chem.* 269:4596–4604 (1994)). Another avenue taken by several investigators has been to incorporate nonhydrolyzable tyrosine phosphate analogs into specific peptide substrates: (1) phosphonomethyl phenylalanine (Zhang et al., *Biochemistry* 33: 2285–2290 (1994)); (2) difluorophosphono-methyl phenylalanine Burk et al., *Synthesis* 11: 1019–1020 (1991)); (3) L-O-malonyltyrosine (Kole et al., *Biochem. Biophys. Res. Commun.* 209: 817–822 (1995)); (4) cinnamic acid (Moran et al., J. Am. Chem. Soc. 117: 10787–10788 (1995); Cao et al., Bioorganic Med. Chem. Lett. 5: 2953–2958 (1995)); (5) sulfotyrosyl (Liotta et al., J. Biol. Chem. 269: 22996–23001 (1994)). A surprising degree of selectivity is observed with simple peptide analogs containing phosphonodifluoromethyl phenylalanine as a substitute for tyrosine (Chen et al., Biochem. Biophys. Res. Commun. 216: 976–984 (1995)). Important information has further been obtained with synthetic peptides containing sulfotyrosyl residues. A synthetic peptide corresponding to the amino acid sequence of a defined loop of the insulin receptor tyrosine kinase, Thr-Arg-Asp-Ile-Xxx-Glu-Thr-Asp-Xxx-Xxx-Arg-Lys (SEQ ID NO:3) (where Xxx denotes sulfotyrosyl), acts as a PTPase inhibitor (Liotta et al., 1994, supra). More importantly, this peptide, when tagged with stearic acid can penetrate cells, and stimulate the action of insulin (Liotta et al., 1994, supra). PTPases: the insulin receptor signaling pathway/diabetes Insulin is an important regulator of different metabolic processes and plays a key role in the control of blood glucose. Defects related to its synthesis or signaling lead to diabetes mellitus. Binding of insulin to its receptor causes rapid (auto)phosphorylation of several tyrosine residues in the intracellular part of the β-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrates (IRS-1) (Wilden et al., J. Biol. Chem. 267: 16660–16668 (1992); Myers and White, Diabetes 42: 643–650 (1993); Lee and Pilch, Am. J. Physiol. 266: C319–C334 (1994); White et al., J. Biol. Chem. 263: 2969–2980 (1988)). The structural basis for the function of the tyrosine-triplet has been provided by recent X-ray crystallographic studies of IRTK that showed tyrosine-1150 to be autoinhibitory in its unphosphorylated state (Hubbard et al., Nature 372: 746–754 (1994)).

Several studies clearly indicate that the activity of the auto-phosphorylated IRTK can be reversed by dephosphorylation in vitro (reviewed in Goldstein, Receptor 3: 1–15 (1993); Mooney and Anderson, J. Biol. Chem. 264: 6850–6857 (1989)), with the tri-phosphorylated tyrosine-1150 domain being the most sensitive target for protein-tyrosine phosphatases (PTPases) as compared to the di- and mono phosphorylated forms (King et al., Biochem. J. 275: 413–418 (1991)). It is, therefore, tempting to speculate that this tyrosine-triplet functions as a control switch of IRTK activity. Indeed, the IRTK appears to be tightly regulated by PTP-mediated dephosphorylation in vivo (Khan et al., J. Biol. Chem. 264: 12931–12940 (1989); Faure et al., J. Biol. Chem. 267: 11215–11221 (1992); Rothenberg et al., J. Biol. Chem. 266: 8302–8311 (1991)). The intimate coupling of PTPases to the insulin signaling pathway is further evidenced by the finding that insulin differentially regulates PTPase activity in rat hepatoma cells (Meyerovitch et al., Biochemistry 31: 10338–10344 (1992)) and in livers from alloxan diabetic rats (Boylan et al., J. Clin. Invest. 90: 174–179 (1992)).

Relatively little is known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., Biochemistry 28: 8864–8871 (1989); Eriksson et al., Diabetologia 39: 235–242 (1995)) and skeletal muscle (Leighton et al., Biochem. J. 276: 289–292 (1991)). In addition, recent studies show that a new class of peroxovanadium compounds act as potent hypoglycemic compounds in vivo (Posner et al.,supra). Two of these compounds were demonstrated to be more potent inhibitors of dephosphorylation of the insulin receptor than of the EGF-receptor.

It was recently found that the ubiquitously expressed SH2 domain containing PTPase, PTP1D (Vogel et al., 1993, supra), associates with and dephosphorylates IRS-1, but apparently not the IR itself (Kuhné et al., J. Biol. Chem. 268:11479–11481 (1993); (Kuhné et al., J. Biol. Chem. 269:15833–15837 (1994)).

Previous studies suggest that the PTPases responsible for IRTK regulation belong to the class of membrane-associated (Faure et al., J. Biol. Chem. 267: 11215–11221 (1992)) and glycosylated molecules (Haring et al., Biochemistry 23: 3298–3306 (1984); Sale, Adv. Prot. Phosphatases 6:159–186 (1991)). Hashimoto et al. have proposed that LAR might play a role in the physiological regulation of insulin receptors in intact cells (Hashimoto et al., J. Biol. Chem. 267: 13811–13814 (1992)). Their conclusion was reached by comparing the rate of dephosphorylation/inactivation of purified IR using recombinant PTP1B as well as the cytoplasmic domains of LAR and PTPα. Antisense inhibition was recently used to study the effect of LAR on insulin signaling in a rat hepatoma cell line (Kulas et al., J. Biol. Chem. 270: 2435–2438 (1995)). A suppression of LAR protein levels by about 60 percent was paralleled by an approximately 150 percent increase in insulin-induced autophosphorylation. However, only a modest 35 percent increase in IRTK activity was observed, whereas the insulin-dependent phosphatidylinositol 3-kinase (PI 3-kinase) activity was significantly increased by 350 percent. Reduced LAR levels did not alter the basal level of IRTK tyrosine phosphorylation or activity. The authors speculate that LAR could specifically dephosphoylate tyrosine residues that are critical for PI 3-kinase activation either on the insulin receptor itself or on a downstream substrate.

While previous reports indicate a role of PTPA in signal transduction through src activation (Zheng et al., Nature 359: 336–339 (1992); den Hertog et al., EMBO J. 12: 3789–3798 (1993)) and interaction with GRB-2 (den Hertog et al., EMBO J. 13: 3020–3032 (1994); Su et al., J. Biol. Chem. 269:18731–18734 (1994)), a recent study suggests a function for this phosphatase and its close relative PTPε as negative regulators of the insulin receptor signal (Møller et al., 1995 supra). This study also indicates that receptor-like PTPases play a significant role in regulating the IRTK, whereas intracellular PTPases seem to have little, if any, activity towards the insulin receptor. While it appears that the target of the negative regulatory activity of PTPases α and ε is the receptor itself, the downmodulating effect of the intracellular TC-PTP seems to be due to a downstream function in the IR-activated signal. Although PTP1B and TC-PTP are closely related, PTP1B had only little influence on the phosphorylation pattern of insulin-treated cells. Both PTPases have distinct structural features that determine their subcellular localization and thereby their access to defined cellular substrates (Frangione et al., Cell 68: 545–560 (1992); Faure and Posner, Glia 9: 311–314 (1993)). Therefore, the lack of activity of PTP1B and TC-PTP towards the IRTK may, at least in part, be explained by the fact that they do not co-localize with the activated insulin receptor. In support of this view, PTP1B and TC-PTP have been excluded as candidates for the IR-associated PTPases in hepatocytes based on subcellular localization studies (Faure et al., J. Biol. Chem. 267: 11215–11221 (1992)).

The transmembrane PTPase CD45, which is believed to be hematopoietic cell-specific, was in a recent study found to negatively regulate the insulin receptor tyrosine kinase in the human multiple myeloma cell line U266 (Kulas et al., *J. Biol. Chem.* 271: 755–760 (1996)).

PTPases: somatostatin

Somatostatin inhibits several biological functions including cellular proliferation (Lamberts et al., *Molec. Endocrinol.* 8:1289–1297 (1994)). While part of the antiproliferative activities of somatostatin are secondary to its inhibition of hormone and growth factor secretion (e.g. growth hormone and epidermal growth factor), other antiproliferative effects of somatostatin are due to a direct effect on the target cells. As an example, somatostatin analogs inhibit the growth of pancreatic cancer presumably via stimulation of a single PTPase, or a subset of PTPases, rather than a general activation of PTPase levels in the cells (Liebow et al., *Proc. Natl. Acad. Sci. U.S.A.* 86: 2003–2007 (1989); Colas et al., *Eur. J. Biochem.* 207: 1017–1024 (1992)). In a recent study it was found that somatostatin stimulation of somatostatin receptors SSTR1, but not SSTR2, stably expressed in CHO-K1 cells can stimulate PTPase activity and that this stimulation is pertussis toxin-sensitive. Whether the inhibitory effect of somatostatin on hormone and growth factor secretion is caused by a similar stimulation of PTPase activity in hormone producing cells remains to be determined.

PTPases: the immune system/autoimmunity

Several studies suggest that the receptor-type PTPase CD45 plays a critical role not only for initiation of T cell activation, but also for maintaining the T cell receptor-mediated signaling cascade. These studies are reviewed in: Weiss A, *Ann. Rev. Genet.* 25: 487–510 (1991); Chan et al., *Annu. Rev. Immunol.* 12: 555–592 (1994); Trowbridge and Thomas, *Annu. Rev. Immunol.* 12: 85–116 (1994).

The exact function of CD45 in lymphocyte activation is currently under intense investigation in many laboratories. Several studies suggest that the PTPase activity of CD45 plays a role in the activation of Lck, a lymphocyte-specific member of the Src family protein-tyrosine kinase (Mustelin et al., *Proc. Natl. Acad. Sci. U.S.A.* 86: 6302–6306 (1989); Ostergaard et al., *Proc. Natl. Acad. Sci. U.S.A.* 86: 8959–8963 (1989)). These authors hypothesized that the phosphatase activity of CD45 activates Lck by dephosphorylation of a C-terminal tyrosine residue, which may, in turn, be related to T-cell activation. In a recent study it was found that recombinant p56$^{lck}$ specifically associates with recombinant CD45 cytoplasmic domain protein, but not to the cytoplasmic domain of the related PTPα (Ng et al., *J. Biol. Chem.* 271: 1295–1300 (1996)). The p56$^{lck}$-CD45 interaction seems to be mediated via a nonconventional SH2 domain interaction not requiring phosphotyrosine. In immature B cells, another member of the Src family protein-tyrosine kinases, Fyn, seems to be a selective substrate for CD45 compared to Lck and Syk (Katagiri et al., *J. Biol. Chem.* 270: 27987–27990 (1995)).

HePTP, a hematopoietic cell specific PTPase, is induced after activation of resting T cells and may play a role in late T cell activation or as a negative regulator of T cell responses (Zanke et al, *Eur. J. Immunol.* 22: 235–239 (1992)). Likewise, the hematopoietic cell specific PTP1C seems to act as a negative regulator and play an essential role in immune cell development. In accordance with the above-mentioned important function of CD45, HePTP and PTP1C, selective PTPase inhibitors may be attractive drug candidates both as immunosuppressors and as immunostimulants. One recent study illustrates the potential of PTPase inhibitors as immunmodulators by demonstrating the capacity of the vanadium-based PTPase inhibitor, BMLOV, to induce apparent B cell selective apoptosis compared to T cells (Schieven et al., *J. Biol. Chem.* 270: 20824–20831 (1995)).

PTPases: cell-cell interactions/cancer

Focal adhesion plaques, an in vitro phenomenon in which specific contact points are formed when fibroblasts grow on appropriate substrates, seem to mimic, at least in part, cells and their natural surroundings. Several focal adhesion proteins are phosphorylated on tyrosine residues when fibroblasts adhere to and spread on extracellular matrix (Gumbiner, *Neuron* 11, 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g. PTPMEG1 (Gu et al., *Proc. Natl. Acad. Sci. U.S.A.* 88: 5867–5871 (1991)), PTPH1 (Yang and Tonks, *Proc. Natl. Acad. Sci. U.S.A.* 88: 5949–5953 (1991)) and PTPD1 (Møller et al., *Proc. Natl. Acad. Sci. U.S.A.* 91: 7477–7481(1994)). The ezrin-like domain show similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., *Proc. Natl. Acad. Sci. U.S.A.* 87:7280–7284(1990)), can inhibit the transforming activity of v-erb and v-fms (Lammers et al., *J. Biol. Chem.* 268: 22456–22462 (1993); Zander et al., *Oncogene* 8:1175–1182 (1993)). Moreover, it was found that transformation by the oncogenic form of the HER2/neu gene was suppressed in NIH 3T3 fribroblasts overexpressing PTP1 B (Brown-Shimer et al., *Cancer Res.* 52: 478–482 (1992)).

The expression level of PTP1B was found to be increased in a mammary cell line transformed with neu (Zhay et al., *Cancer Res.* 53:2272–2278 (1993)). The intimate relationship between tyrosine kinases and PTPases in the development of cancer is further evidenced by the recent finding that PTPε is highly expressed in murine mammary tumors in transgenic mice over-expressing c-neu and v-Ha-ras, but not c-myc or int-2 (Elson and Leder, *J. Biol. Chem.* 270:26116–26122 (1995)). Further, the human gene encoding PTPγ was mapped to 3p21, a chromosomal region which is frequently deleted in renal and lung carcinomas (LaForgia et al., *Proc. Natl. Acad. Sci. U.S.A.* 88: 5036–5040 (1991)).

In this context, it seems significant that PTPases appear to be involved in controlling the growth of fibroblasts. In a recent study it was found that Swiss 3T3 cells harvested at high density contain a membrane-associated PTPase whose activity on an average is 8-fold higher than that of cells harvested at low or medium density (Pallen and Tong, *Proc. Natl. Acad. Sci. U.S.A.* 88: 6996–7000 (1991)). It was hypothesized by the authors that density-dependent inhibition of cell growth involves the regulated elevation of the activity of the PTPase(s) in question. In accordance with this view, a novel membrane-bound, receptor-type PTPase, DEP-1, showed enhanced (>=10-fold) expression levels with increasing cell density of WI-38 human embryonic lung fibroblasts and in the AG1518 fibroblast cell line (Östman et al., *Proc. Natl. Acad. Sci. U.S.A.* 91: 9680–9684 (1994)).

Two closely related receptor-type PTPases, PTPκ and PTPμ, can mediate homophilic cell-cell interaction when expressed in non-adherent insect cells, suggesting that these PTPases might have a normal physiological function in cell-to-cell signaling (Gebbink et al., *J. Biol. Chem.* 268: 16101–16104 (1993); Brady-Kalnay et al., *J. Cell Biol.* 122: 961–972 (1993); Sap et al., *Mol. Cell. Biol.* 14: 1–9 (1994)). Interestingly, PTPκ and PTPμ do not interact with each other, despite their structural similarity (Zondag et al., *J. Biol. Chem.* 270: 14247–14250 (1995)). From the studies described above it is apparent that PTPases may play an important role in regulating normal cell growth. However, as pointed out above, recent studies indicate that PTPases may also function as positive mediators of intracellular signaling and thereby induce or enhance mitogenic responses. Increased activity of certain PTPases might therefore result in cellular transformation and tumor formation. Indeed, in one study over-expression of PTPα was found to lead to transformation of rat embryo fibroblasts (Zheng, supra). In addition, a novel PTP, SAP-1, was found to be highly expressed in pancreatic and colorectal cancer cells. SAP-1 is mapped to chromosome 19 region q13.4 and might be related to carcinoembryonic antigen mapped to 19q13.2 (Uchida et al., *J. Biol. Chem.* 269: 12220–12228 (1994)). Further, the dsPTPase, cdc25, dephosphorylates cdc2 at Thr14/Tyr-15 and thereby functions as positive regulator of mitosis (reviewed by Hunter, *Cell* 80:225–236 (1995)). Inhibitors of specific PTPases are therefore likely to be of significant therapeutic value in the treatment of certain forms of cancer.

PTPases: platelet aggregation

Recent studies indicate that PTPases are centrally involved in platelet aggregation. Agonist-induced platelet activation results in calpain-catalyzed cleavage of PTP1B with a concomitant 2-fold stimulation of PTPase activity (Frangioni et al., *EMBO J.* 12: 4843–4856 (1993)). The cleavage of PTP1B leads to subcellular relocation of the enzyme and correlates with the transition from reversible to irreversible platelet aggregation in platelet-rich plasma. In addition, the SH2 domain containing PTPase, PTP1C/SH-PTP1, was found to translocate to the cytoskeleton in platelets after thrombin stimulation in an aggregation-dependent manner (Li et al., *FEBS Lett.* 343: 89–93 (1994)).

Although some details in the above two studies were recently questioned there is over-all agreement that PTP1B and PTP1C play significant functional roles in platelet aggregation (Ezumi et al., *J. Biol. Chem.* 270:11927–11934 (1995)). In accordance with these observations, treatment of platelets with the PTPase inhibitor pervanadate leads to significant increase in tyrosine phosphorylation, secretion and aggregation (Pumiglia et al., *Biochem. J.* 286: 441–449 (1992)).

PTPases: osteoporosis

The rate of bone formation is determined by the number and the activity of osteoblasts, which in term are determined by the rate of proliferation and differentiation of osteoblas progenitor cells, respectively. Histomorphometric studies indicate that the osteoblast number is the primary determinant of the rate of bone formation in humans (Gruber et al., *Mineral Electrolyte Metab.* 12: 246–254 (1987); reviewed in Lau et al., *Biochem. J.* 257: 23–36 (1989)). Acid phosphatases/PTPases may be involved in negative regulation of osteoblast proliferation. Thus, fluoride, which has phosphatase inhibitory activity, has been found to increase spinal bone density in osteoporotics by increasing osteoblast proliferation (Lau et al., supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985); Lau et al., *J. Biol. Chem.* 262: 1389–1397 (1987); Lau et al., *Adv. Protein Phosphatases* 4: 165–198 (1987)). Interestingly, it was recently found that the level of membrane-bound PTPase activity was increased dramatically when the osteoblast-like cell line UMR 106.06 was grown on collagen type-I matrix compared to uncoated tissue culture plates. Since a significant increase in PTPase activity was observed in density-dependent growth arrested fibroblasts (Pallen and Tong, *Proc. Natl. Acad. Sci.* 88: 6996–7000 (1991)), it might be speculated that the increased PTPase activity directly inhibits cell growth. The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the recent identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. It may be hypothesized that PTPase inhibitors may prevent differentiation via inhibition of OST-PTP or other PTPases thereby leading to continued proliferation. This would be in agreement with the above-mentioned effects of fluoride and the observation that the tyrosine phosphatase inhibitor orthovanadate appears to enhance osteoblast proliferation and matrix formation (Lau et al., *Endocrinology* 116: 2463–2468 (1988)). In addition, it was recently observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)).

PTPases: microorganisms

Dixon and coworkers have called attention to the fact that PTPases may be a key element in the pathogenic properties of Yersinia (reviewed in Clemens et al. *Molecular Microbiology* 5: 2617–2620 (1991)). This finding was rather surprising since tyrosine phosphate is thought to be absent in bacteria. The genus Yersinia comprises 3 species: *Y. pestis* (responsible for the bubonic plague), *Y. pseudoturberculosis* and *Y. enterocolitica* (causing enteritis and mesenteric lymphadenitis). Interestingly, a dual-specificity phosphatase, VH1, has been identified in Vaccinia virus (Guan et al., *Nature* 350: 359–263 (1991)). These observations indicate that PTPases may play critical roles in microbial and parasitic infections, and they further point to PTPase inhibitors as a novel, putative treatment principle of infectious diseases.

SUMMARY OF THE INVENTION

The inventors have identified a novel class of compounds that has the capacity to modulate the activity of molecules with tyrosine recognition units, including PTPases, preferably a selective modulation. In one aspect, the present invention relates to novel acrylic acids of general formula (I)

$$(L)_n\text{—}Ar_1\text{—}CH\text{=}CH\text{—}COOR_1 \qquad (I)$$

wherein $(L)_n$, n, $Ar_1$, and $R_1$ are defined as below.

DETAILED DESCRIPTION OF THE INVENTION

The present invention relates to novel acrylic acids of formula (I)

$$(L)_n-Ar_1-CH=CH-COOR_1 \qquad (I)$$

wherein n is 1, 2, 3, 4, or 5 and (L)$_n$ represents up to five (5) substituents which independently of each other are hydrogen, $C_{1-6}$-alkyl, $C_{1-6}$-alkoxy, hydroxy, halogen, trihalogenomethyl, hydroxy-$C_{1-6}$-alkyl, amino-$C_{1-6}$-alkyl, $COR_2$, $NO_2$, CN, CHO, $C_{1-6}$-alkanoyloxy, carbamoyl, $NR_5R_6$, aryloxy optionally substituted; $R_2$ is $C_{1-6}$-alkyl, aryl optionally substituted, aralkyl optionally substituted, OH, $NR_3R_4$ wherein $R_3$ and $R_4$ independently of each other are hydrogen, $C_{1-6}$-alkyl, aryl optionally substituted, aralkyl optionally substituted;

$R_5$ and $R_6$ are independently of each other hydrogen, $C_{1-6}$alkyl, aryl optionally substituted, aralkyl optionally substituted or $COZ_1$ wherein $Z_1$ is $C_{1-6}$-alkyl, aryl optionally substituted, aralkyl optionally substituted;

L is $A-Y_1-(W_1)-X-(W_2)-Y_2$ wherein X is a chemical bond, CO, $CONR_7$, $NR_7CO$, $NR_7$, O, S, SO, or $SO_2$;

$Y_1$ and $Y_2$ are independently a chemical bond, O, S, or $NR_7$;

$R_7$ is hydrogen, $C_{1-6}$-alkyl, aryl optionally substituted, aralkyl optionally substituted, heteroaryl optionally substituted, $COZ_2$ wherein $Z_2$ is $C_{1-6}$-alkyl, aryl optionally substituted, aralkyl optionally substituted;

$W_1$ and $W_2$ are independently a chemical bond or saturated or unsaturated $C_{1-6}$-alkylene;

A is aryl optionally substituted, heteroaryl optionally substituted, biaryl optionally substituted, arylheteroaryl optionally substituted, $NR_8R_9$ wherein $R_8$ and $R_9$ independently are hydrogen, $C_{1-6}$-alkyl, aryl optionally substituted, aralkyl optionally substituted, heteroaryl optionally substituted, $COZ_3$ wherein Z is $C_{1-6}$-alkyl, aryl optionally substituted, aralkyl optionally substituted, heteroaryl optionally substituted or when $R_8$ and $R_9$ together with the nitrogen atom forms a ring system A is a saturated or partially saturated heterocyclic ring system optionally substituted with $C_{1-6}$-alkyl, aryl optionally substituted, aralkyl optionally substituted, heteroaryl optionally substituted, OH, $C_{1-6}$-alkoxy, hydroxy-$C_{1-6}$-alkyl, amino-$C_{1-6}$-alkyl, $COZ_4$ wherein $Z_4$ is OH, $C_{1-6}$-alkyl, $NR_{10}R_{11}$ wherein $R_{10}$ and $R_{11}$ independently are hydrogen, $C_{1-6}$alkyl; $R_1$ is hydrogen, $C_{1-6}$alkyl, aryl optionally substituted, aralkyl optionally substituted;

and $Ar_1$ is aryl or heteroaryl;

or a pharmaceutically acceptable salt thereof.

In the above-mentioned formula (I) aryl, heteroaryl, $Ar_1$ and A are exemplified by the following examples. Specific examples of the aryl and biaryl residues include phenyl, biphenyl, indene, fluorene, naphthyl (1-naphthyl, 2-naphthyl), anthracene (1-anthracenyl, 2-anthracenyl, 3-anthracenyl). Specific examples of the heteroaryl include pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3- pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl, (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), 5-oxo-10,11-dihydro-5H-dibenzo[a,d]cyclo-hepten-1-yl, 5-oxo-10,11-dihydro-5H-dibenzo[a,d]cyclohepten-2-yl, 5-oxo-10,11-dihydro-5H-dibenzo[a,d]cyclohepten-3-yl, 5-oxo-10,11-dihydro-5H-dibenzo[a,d]cyclohepten-4-yl, piperidinyl (2-piperidinyl, 3-piperidinyl, 4-piperidinyl), pyrrolidinyl (1-pyrrolidinyl, 2-pyrrolidinyl, 3-pyrrolidinyl), morpholinyl (1-morpholinyl, 2-morpholinyl), piperazinyl (1-piperazinyl).

Specific examples of the arylheteroaryl residue include phenylpyridyl (2-phenylpyridyl, 3-phenylpyridyl, 4-phenylpyridyl), phenylpyrimidinyl (2-phenylpyrimidinyl, 4-phenylpyrimidinyl, 5-phenylpyrimidinyl, 6-phenylpyrimidinyl), phenylpyrazinyl, phenylpyridazinyl (3-phenyl-pyridazinyl, 4-phenylpyridazinyl, 5-phenylpyridazinyl).

In the above mentioned compound of formula (I) examples of L is quinolinyl-piperazinylethyl such as 2-4-quinolin-2-yl-piperazin-1-yl)ethyl, biphenyloxymethyl such as biphenyl-4-yloxymethyl, phenyl-piperazinylmethyl such as 4-phenylpiperazin-1-ylmethyl, biphenylmethyl such as 1-biphenyl-4-ylmethyl.

The $C_{1-6}$-alkyl residues include aliphatic hydrocarbon residues, unsaturated aliphatic hydrocarbon residues, alicyclic hydrocarbon residues. Examples of the aliphatic hydrocarbon residues include saturated aliphatic hydrocarbon residues having 1 to 6 carbon atoms such as methyl, ethyl, n-propyl, isopropyl, n-butyl, isobutyl, sec.butyl, tert.butyl, n-pentyl, isopentyl, neopentyl, tert.pentyl, n-hexyl, isohexyl.

Example of the unsaturated aliphatic hydrocarbon residues include those having 2 to 6 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, ethynyl, 1-propionyl, 2-propionyl, 1-butynyl, 2-butynyl, 3-butynyl, 1-pentynyl, 2-pentenyl, 3-pentenyl, 4-pentenyl, 1-hexynyl, 3-hexynyl, 2,4hexadiynyl, 5-hexynyl. Examples of the alicyclic hydrocarbon residue include saturated alicyclic hydrocarbon residues having 3 to 6 carbon atoms such as cyclopropyl, cyclobutyl, cyclopentyl, cyclohexyl; and $C_{5-6}$ unsaturated alicyclic hydrocarbon residues having 5 to 6 carbon atoms such as 1 cyclopentenyl, 2-cyclopentenyl, 3-cyclopentenyl, 1-cyclohexenyl, 2-cyclohexenyl, 3-cyclohexenyl.

The $C_{1-6}$-alkoxy residues include aliphatic hydrocarbon residues connected to an oxygene atom. Examples of the aliphatic hydrocarbon residues include saturated aliphatic hydrocarbon residues having 1 to 6 carbon atoms such as methoxy, ethoxy, propoxy, iso-propoxy, butoxy, isobutoxy, sec.butoxy, tert.butoxy, pentoxy, isopentoxy, neopentoxy, tert.pentoxy, hexyloxy, isohexyloxy.

The $C_{1-6}$-alkoxycarbonyl residues include a $C_{1-6}$-alkoxy residue connected to a carbonyl residue such as methoxycarbonyl, ethoxy-carbonyl, propoxycarbonyl, and tert-butoxycarbonyl.

The $C_{1-6}$-alkanoyloxy residues include a acyl residue connected to an oxygen atom wherein the acyl residue is an aliphatic hydrocarbon residues connected to an carbonyl residue such as acetyloxy, propionyloxy, isopropionyloxy.

The aralkyl residue include an aryl residue connected to an $C_{1-6}$-alkyl residue e.g. phenyl alkyls having 7 to 9 carbon atoms such as benzyl, phenethyl, 1-phenylethyl, 3-phenylpropyl, 2-phenylpropyl and 1-phenylpropyl; and naphthyl alkyl having 11 to 13 carbon atoms such as 1-naphthylmethyl, 1-naphthylethyl, 2-naphthylmethyl, and 2-naphthylethyl.

Aryloxy include an aryl connected to an oxygen atom such as phenyloxy, naphthyloxy.

Aralkyloxy include an aralkyl connected to an oxygen atom such as benzyloxy, phenethyloxy, naphthylmethyloxy.

Biaryl include an aryl connected to an aryl residue such as biphenyl, 1-phenyinaphthyl, 2-phenylnaphthyl.

Biaryloxy include an biaryl connected to an oxygen atom such as biphenyl ether, 1-naphthylphenyl ether, 2-naphthylphenyl ether.

The heteroaryl residue is a 5- or 6-membered aromatic ring, which can be fused to one or more phenyl rings and contains, besides carbon atoms, 1 to 4 atoms selected from N, O, and S as atoms constituting the ring, which is bonded through carbon atoms such as defined above.

The halogen residue include fluorine, chlorine, bromine, and iodine.

The term "optionally substituted" means an aryl residue, a heteroaryl residue, or a $C_{1-6}$-alkyl residue that may be unsubstituted or may have 1 or more preferably 1 to 5 substituents, which are the same as or different from one another. Examples of these substituents include, halogen (fluorine, chlorine, bromine, iodine), hydroxyl, cyano, nitro, trifluoromethyl, carbamoyl, $C_{1-4}$-acyl (e.g. acetyl, propionyl, isopropionyl), $C_{1-6}$-alkoxy (e.g. methoxy, ethoxy, propoxy, isopropoxy, butoxy, and tert.butoxy), $C_{1-6}$-alkyl (e.g. methyl, ethyl, propyl, cyclopropyl, isopropyl, butyl, and tert.butyl), $C_{1-6}$-alkoxycarbonyl (e.g. ones having 2 to 6 carbon atoms such as methoxycarbonyl, ethoxycarbonyl, and propoxycarbonyl), $C_{1-6}$-alkanoyloxy (e.g. ones having 2 to 6 carbon atoms such as acetyloxy, propionyloxy, isopropionyloxy), $C_{1-4}$-alkylthio (e.g. ones having 1 to 4 carbon atoms such as methylthio, ethylthio, propylthio, and isopropylthio), $C_{1-4}$-alkylamino (e.g. one having 1 to 4 carbon atoms such as methylamino, ethylamino, dimethylamino, and 1-pyrrolidinyl), heteroaryl (as exemplified above), aryloxy (e.g. phenyloxy), and a aralkloxy (e.g. benzyloxy).

The compounds of formula (I) may exist as geometric and optical isomers and all isomers and mixtures thereof are included herein. Isomers may be separated by means of standard methods such as chromatographic techniques or fractionated crystallisation of e.g. suitable salts.

The compounds according to the invention may optionally exist as pharmaceutically acceptable salts comprising acid addition salts or metal salts or—optionally alkylated—ammonium salts.

Examples of such salts include the alkali metal or amine salts of 1H- or 2H-tetrazoles of this invention, such as the sodium, potassium, $C_{1-6}$-alkylamine, di ($C_{1-6}$-alkyl) amine, tri ($C_{1-6}$-alkyl) amine and the four (4) corresponding omega-hydroxy analogues (e.g. methylamine, ethylamine, propylamine, dimethylamine, diethylamine, dipropylamine, trimethylamine, triethylamine, tripropylamine, di(hydroxyethyl)amine, and the like;

inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in *Journal of Pharmaceutical Science* 66: 2 (1977) which are hereby incorporated by reference.

The compounds of formula (I) may be prepared by art-recognised procedures from known compounds or readily preparable intermediates. An exemplary general procedure is as follows:

Method A:

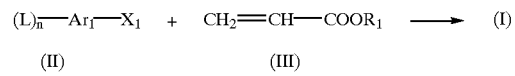

$$(L)_{\overline{n}}—Ar_1—X_1 \quad + \quad CH_2{=\!=\!=}CH—COOR_1 \quad \longrightarrow \quad (I)$$

$$(II) \qquad\qquad\qquad (III)$$

By allowing a compound of formula (II), wherein $(L)_n$, n, and $Ar_1$ are as defined above and $X_1$ is a suitable leaving group such as bromo, iodo or triflate to react with a compound of formula (III) wherein $R_1$ is defined as above.

These reactions may be carried out in a solvent such as triethylamine (TEA), methanol, ethanol or dimethylsulfoxide (DMSO) in the presence of a palladium catalyst, e.g. (Pd/C, Pd/Al$_2$O$_3$, Pd/BaSO$_4$, Pd/SiO$_2$ or Pd(OAc)$_2$) and a triaryl-phosphine catalyst as e.g. (triphenyl-phosphine or tri-o-tolyl-phosphine) at temperatures ranging from 50° C. to 150° C. for 1 to 60 hours.

Method B:

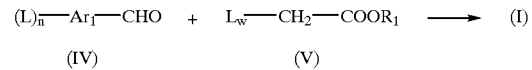

$$(L)_{\overline{n}}—Ar_1—CHO \quad + \quad L_w—CH_2—COOR_1 \quad \longrightarrow \quad (I)$$

$$(IV) \qquad\qquad\qquad (V)$$

By allowing a compound of formula (IV), wherein $(L)_n$, n, and $Ar_1$ are as defined above to react with a compound of formula (V) wherein $R_1$ is as defined above and $L_w$ is trimethylsilyl (a Peterson reaction), triphenylphosphonium (a Wittig reaction), diethyl phosphate (a modified Wittig reaction) or carbonyloxy$C_{1-6}$-alkyl (e.g. COOEt or COOMe);

These reactions may be carried out in a solvent such as methanol, ethanol, tetrahydrofuran (THF), toluene, N,N- dimethylformamide (DMF) or dimethylsulfoxide (DMSO) in the presence of a base such as triethylamine, pyridine, piperidine, sodium hydride, sodium methoxide, sodium ethoxide, sodium hydroxide, potassium tert-butoxide, lithium diisopropylamide at temperatures ranging from −50° C. to 150° C. for 1 to 60 hours.

Compounds of formula (II), (III) (IV) or (V) may be prepared by methods familiar to those skilled in the art or may be commercially available.

Under certain circumstances it may be necessary to protect the intermediates used in the above methods. Introduction and removal of such groups is e.g. described in "Protective Groups in Organic Synthesis" T. W. Greene and P. G. M. Wuts, ed. Second edition (1991).

In preferred embodiments, the compounds of the invention modulate the activity of protein tyrosine phosphatases or other molecules with phosphotyrosine recognition unit(s).

In one preferred embodiment the compounds of the invention act as inhibitors of PTPases, e.g. protein tyrosine phosphatases involved in regulation of tyrosine kinase signaling pathways. Preferred embodiments include modulation of receptor-tyrosine kinase signaling pathways via interaction with regulatory PTPases, e.g. the signaling pathways of the insulin receptor, the IGF-I receptor and other members of the insulin receptor family, the EGF-receptor family, the platelet-derived growth factor receptor family, the nerve growth factor receptor family, the hepatocyte growth factor receptor family, the growth hormone receptor family and members of other receptor-type tyrosine kinase families. Further preferred embodiments of the inventions is modulation of non-receptor tyrosine kinase signaling through modulation of regulatory PTPases, e.g. modulation of members of the Src kinase family. One type of preferred embodiments of the inventions relate to modulation of the activity of PTPases that negatively regulate signal transduction pathways. Another type of preferred embodiments of the inventions relate to modulation of the activity of PTPases that positively regulate signal transduction pathways.

In a preferred embodiment the compounds of the invention act as modulators of the active site of PTPases. In another preferred embodiment the compounds of the invention modulate the activity of PTPases via interaction with structures positioned outside of the active sites of the enzymes, preferably SH2 domains. Further preferred embodiments include modulation of signal transduction pathways via binding of the compounds of the invention to SH2 domains or PTB domains of non-PTPase signaling molecules.

Other preferred embodiments include use of the compounds of the invention for modulation of cell-cell interactions as well as cell-matrix interactions.

As a preferred embodiment, the present invention include within its scope pharmaceutical compositions comprising, as an active ingredient, at least one of the compounds of formula (I) in association with a pharmaceutical carrier or diluent Optionally, the pharmaceutical composition can comprise at least one of the compounds of formula (I) combined with compounds exhibiting a different activity, e.g. an antibiotic or other pharmacologically active material.

As a preferred embodiment, the compounds of the invention may be used as therapeuticals to inhibit of PTPases involved in regulation of the insulin receptor tyrosine kinase signaling pathway in patients with type I diabetes, type II diabetes, impaired glucose tolerance, insulin resistance, and obesity. Further preferred embodiments include use of the compounds of the invention for treatment of disorders with general or specific dysfunctions of PTPase activity, e.g. proliferarive disorders such as psoriasis and neoplastic diseases. As another embodiment, the compounds of the invention may be used in pharmaceutical preparations for treatment of osteoporosis.

Preferred embodiments of the invention further include use of compound of formula (I) in pharmaceutical preparations to increase the secretion or action of growth hormone and its analogs or somatomedins including IGF-1 and IGF-2 by modulating the activity of PTPases or other signal transduction molecules with affinity for phosphotyrosine involved controlling or inducing the action of these hormones or any regulating molecule.

To those skilled in the art, it is well known that the current and potential uses of growth hormone in humans are varied and multitudinous. Thus, compounds of the invention can be administered for purposes of stimulating the release of growth hormone from the pituitary or increase its action on target tissues thereby leading to similar effects or uses as growth hormone itself. The uses of growth hormone may be summarized as follows: stimulation of growth hormone release in the elderly; prevention of catabolic side effects of glucocorticoids; treatment of osteoporosis, stimulation of the immune system; treatment of retardation, acceleration of wound healing; accelerating bone fracture repair, treatment of growth retardation; treating renal failure or insufficiency resulting in growth retardation; treatment of physiological short stature including growth hormone deficient children and short stature associated with chronic illness; treatment of obesity and growth retardation associated with obesity; treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondro-dysplasias, Noonans syndrome, schizophrenia, depressions, Alzheimer's disease, delayed wound healing and psychosocial deprivation; treatment of pulmonary dysfunction and ventilator dependency; attenuation of protein catabolic responses after major surgery; reducing cachexia and protein loss due to chronic illness such as cancer or AIDS; treatment of hyperinsulinemia including nesidio-blastosis; Adjuvant treatment for ovulation induction; stimulation of thymic development and prevention the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling and cartilage growth; stimulation of the immune system in companion animals and treatment of disorder of aging in companion animals; growth promotant in livestock and stimulation of wool growth in sheep.

The compounds of the invention may be used in pharmaceutical preparations for treatment of various disorders of the immune system, either as a stimulant or suppressor of normal or perturbed immune functions, including autoimmune reactions. Further embodiments of the invention include use of the compounds of the invention for treatment of allergic reactions, e.g. asthma, dermal reactions, conjunctivitis.

In another embodiment compounds of the invention may be used in pharmaceutical preparations for prevention or induction of platelet aggregation.

In yet another embodiment, compounds of the invention may be used in pharmaceutical preparations for treatment of infectious disorders. In particular, the compounds of the invention may be used for treatment of infectious disorders caused by Yersinia and other bacteria as well as disorders caused by viruses or other micro-organisms.

Compounds of the invention may additionally be used for treatment or prevention of diseases in animals, including commercially important animals.

Also included in the present invention is a process for isolation of PTPases via affinity purification procedures based on the use of immobilized compounds of the invention using procedures well-known to those skilled in the art.

The invention is further directed to a method for detecting the presence of PTPases in cell or in a subject comprising:

(a) contacting said cell or an extract thereof with labeled compounds of the invention.

(b) detecting the binding of the compounds of the invention or measuring the quantity bound, thereby detecting the presence or measuring the quantity of certain PTPases.

The invention further relates to analysis and identification of the specific functions of certain PTPases by modulating their activity by using compounds of the invention in cellular assay systems or in whole animals.

DEFINITIONS

Signal transduction is a collective term used to define all cellular processes that follow the activation of a given cell or tissue. Examples of signal transduction, which are not intended to be in any way limiting to the scope of the invention claimed, are cellular events that are induced by polypeptide hormones and growth factors (e.g. insulin, insulin-like growth factors I and II, growth hormone, epidermal growth factor, platelet-derived growth factor), cytokines (e.g. inter-leukins), extracellular matrix components, and cell-cell interactions.

Phosphotyrosine recognition units/tyrosine phosphate recognition units/pTyr recognition units are defined as areas or domains of proteins or glycoproteins that have affinity for molecules containing phosphorylated tyrosine residues (pTyr). Examples of pTyr recognition units, which are not intended to be in any way limiting to the scope of the invention claimed, are: PTPases, SH2 domains and PTB domains.

PTPases are defined as enzymes with the capacity to dephosphorylate pTyr-containing proteins or glycoproteins. Examples of PTPases, which are not intended to be in any way limiting to the scope of the invention claimed, are: 'classical' PTPases (intracellular PTPases (e.g. PTP1B, TC-PTP, PTP1C, PTP1D, PTPD1, PTPD2) and receptor-type PTPases (e.g. PTPα, PTPε, PTPβ, PTPγ, CD45, PTPζ, PTPλ), dual specificity phosphatases (VH1, VHR, cdc25), LMW-PTPases or acid phosphatases.

Modulation of cellular processes is defined as the capacity of compounds of the invention to 1) either increase or decrease ongoing, normal or abnormal, signal transduction, 2) initiate normal signal transduction, and 3) initiate abnormal signal transduction.

Modulation of pTyr-mediated signal transduction/modulation of the activity of molecules with pTyr recognition units is defined as the capacity of compounds of the invention to 1) increase or decrease the activity of proteins or glycoproteins with pTyr recognition units (e.g. PTPases, SH2 domains or PTB domains) or to 2) decrease or increase the association of a pTyr-containing molecule with a protein or glyco-protein with pTyr recognition units either via a direct action on the pTyr recognition site or via an indirect mechanism. Examples of modulation of pTyr-mediated signal transduction/modulation of the activity of molecules with pTyr recognition units, which are not intended to be in any way limiting to the scope of the invention claimed, are: a) inhibition of PTPase activity leading to either increased or decreased signal transduction of ongoing cellular processes; b) inhibition of PTPase activity leading to initiation of normal or abnormal cellular activity; c) stimulation of PTPase activity leading to either increased or decreased signal transduction of ongoing cellular processes; d) stimulation of PTPase activity leading to initiation of normal or abnormal cellular activity; e) inhibition of binding of SH2 domains or PTB domains to proteins or glycoproteins with pTyr leading to increase or decrease of ongoing cellular processes; f) inhibition of binding of SH2 domains or PTB domains to proteins or glycoproteins with pTyr leading to initiation of normal or abnormal cellular activity.

A subject is defined as any mammalian species, including humans.

Pharmacological Methods

For the above indications the dosage will vary depending on the compound of formula (1) employed, on the mode of administration and on the therapy desired. However, in general, satisfactory results are obtained with a dosage of from about 0.5 mg to about 1000 mg, preferably from about 1 mg to about 500 mg of compounds of formula (I), conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula (I) admixed with a pharmaceutical carrier or diluent.

The compounds of formula (I) may be administered in a pharmaceutically acceptable acid addition salt form or where possible as a metal or a $C_{1-6}$-alkylammonium salt. Such salt forms exhibit approximately the same order of activity as the free acid forms.

This invention also relates to pharmaceutical compositions comprising a compound of formula (I) or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC approx. | 9 mg |
| *Mywacett ® 9-40 T approx. | 0.9 mg |

*Acylated monoglyceride used as plasticiser for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

Additionally the compounds of formula I may be useful in vitro and/or in vivo diagnostic tools.

EXAMPLES

The process for preparing compounds of formula (I) and preparations containing them is further illustrated in the following examples, which, however, are not to be construed as limiting.

Hereinafter, TLC is thin layer chromatography, CDCl$_3$ is deuterio chloroform and DMSO-d$_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm) downfield from tetramethylsilane as internal reference standard. M.p. is melting point and is given in °C and is not corrected. Column chromatography was carried out using the technique described by W. C. Still et al., *J. Org. Chem.* 43:2923 (1978) on Merck silica gel 60 (Art. 9385). HPLC analyses were performed using 5 µm C18 4×250 mm column eluted with various mixtures of water and acetonitrile, flow=1 ml/min, as described in the experimental section.

Compounds used as starting materials are either known compounds or compounds which can readily be prepared by methods known per se.

EXAMPLE 1
3-(3-(Biphenyl-4-yloxymethyl)phenyl)acrylic acid

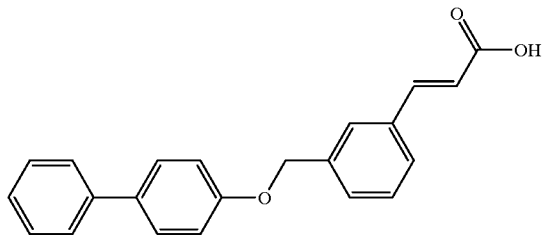

To a solution of 4-phenylphenol (6.13 g, 36 mmol) in dry N,N-dimethyl-formamide (100 ml) kept under an atmosphere of nitrogen, sodium hydride (1.73 g, 43.2 mmol, 60% dispersion in mineral oil) was added in portions and the reaction mixture was stirred until gas evolution ceased. 3-Bromobenzyl bromide (10.0 g, 39.61 mmol) was added in portions and the reaction mixture was stirred at room temperature for 18 h. To the reaction mixture water (50 ml) was added. The precipitate was filtered off and washed with water (3×100 ml), 96% ethanol (2×30 ml), diethyl ether (2×80 ml), and dried in vacuo at 50° C. for 18 h affording 11.64 g (95 %) of 4-(3-bromo-benzyloxy)biphenyl as a solid.

A mixture of the above biphenyl (5.0 g, 14.74 mmol), tert-butyl acrylate (2.98 ml, 19.16 mmol), palladium acetate (33 mg, 0.15 mmol), tri-ortho-tolylphosphine (180 mg, 0.59 mmol) in triethylamine (20 ml) under an atmosphere of nitrogen was stirred at 100° C. for 18 h in an ampoule. The cooled reaction mixture was diluted with toluene (100 ml) and the solid filtered off. The organic phase was washed with water (3×60 ml), dried (MgSO$_4$), filtered and evaporated in vacuo affording 5.69 g of a solid which was suspended in a mixture of heptane (80 ml) and diethyl ether (15 ml) and stirred for 18 h at room temperature. The solid was filtered off and washed with heptane and with a mixture of heptane and diethyl ether (95:5), dried in vacuo at 50° C. for 3 h affording 4.53 g (80 %) of 3-(3-(biphenyl4-yloxymethyl) phenyl)acrylic acid tert-butyl ester as a solid.

TLC: R$_f$=0.52 (SiO$_2$: ethyl acetate/heptane=1:4) $^1$H NMR (200 MHz, CDCl$_3$) $\delta_H$ 1.55 (s, 9H), 5.12 (s, 2H), 6.41 (d, 1H, J$_H$=14.6 Hz), 7.05 (m, 2H), 7.31–7.66 (m, 12H).

To a solution of the above tert-butyl ester (4.0 g, 10.35 mmol) in-dichloromethane (50 ml) was added trifluoroacetic acid (5 ml) and the reaction mixture was stirred for 5 h at room temperature. An additional 5 ml of trifluoroacetic acid was added and the reaction mixture was stirred for 60 h at room temperature. The precipitate was filtered off and washed with dichloromethane (2×20 ml), diethyl ether (2×20 ml) and dried in vacuo at 50° C. for 10 h affording 2.78 g (81%) of the title compound as a solid.

Calculated for C$_{22}$H$_{18}$O$_3$: C, 79.98%; H, 5.49%. Found: C, 80.44%; H, 5.59%. HPLC retention time=31.80 minutes. (water/acetonitrile 1:1, 0.01 N (NH$_4$)$_2$SO$_4$ buffer, pH=2.5) $^1$H NMR (200 MHz, DMSO-d$_6$): $\delta_H$ 5.17 (s, 2H), 6.57 (d, 1H, J$_H$=16.02 Hz), 7.11 (m, 2H), 7.26–7.68 (m, 11 H), 7.79 (s,1 H), 12.46 (bs, 1 H).

EXAMPLE 2
3-(2-(4-Phenyl-piperazin-1-ylmethyl)-phenyl)acrylic acid

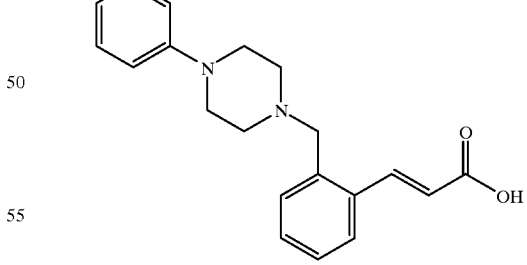

2-Bromobenzyl bromide (10.20 g, 0.04 mol) was dissolved in dry N,N-dimethylformamide (100 ml), 1-phenylpiperazine (6.83 g, 0.04 mol) and potassium carbonate (16.59 g, 0.12 mol) were added. The mixture was stirred at room temperature for 24 h. The mixture was poured into water (250 ml) and extracted with ethyl acetate (3×50 ml). The combined organic extracts were washed with water (3×50 ml), brine (50 ml), dried (MgSO$_4$) and evaporated in vacuo. The solid reminder was washed with heptane and filtered off and dried in vacuo affording 13.1 g (99%) of 1-(2-bromo-benzyl)-4-phenyl-piperazine as a solid.

TLC: $R_f$=0.48 (Ethyl acetate/heptane 1:4)

A mixture of the above piperazine (4.88 g, 14.7 mmol), tert-butyl acrylate (2.80 ml, 19.1 mmol), palladium acetate (33 mg, 0.15 mmol), tri-ortho-tolyl phosphine (180 mg, 0.59 mmol) in triethylamine (20 ml) under an atmosphere of nitrogen was stirred at 100° C. for 24 h in an ampoule. The cooled reaction mixture was diluted with toluene (150 ml) and the solid filtered off. The organic phase was washed with water (3×60 ml), brine (50 ml), dried (MgSO$_4$), filtered and evaporated in vacuo affording a solid which was suspended in heptane (80 ml) and stirred at room temperature. The solid was filtered off and washed with heptane, dried in vacuo at 50° C. for 3 h affording 1.18 g (26%) of 3-2-4-phenyl-piperazin-1-ylmethyl)-phenyl)acrylic acid tert-butyl ester as a solid. By cooling the heptane phase an additional 3.4 g (74%) of 3-(2-(4-phenylpiperazin-1-ylmethyl)-phenyl) acrylic acid tert-butyl ester was obtained.

TLC: $R_f$=0.33 (SiO$_2$: ethyl acetate/heptane=1:4) $^1$H NMR (200 MHz, CDCl$_3$): $\delta_H$ 1.53 (s, 9H), 2.62 (m, 4H), 3.17 (m, 4H), 3.65 (s, 2H), 6.30 (d, 1 H, $J_H$=16.01 Hz), 6.87 (m, 3H), 7.28 (m, 5H), 7.59 (m, 1H), 8.15 (d, 1H, $J_H$=16.01 Hz).

To a solution of the above tert-butyl ester (3.35 g, 10.7 mmol) in dichloromethane (35 ml) was added trifluoroacetic acid (6.0 ml) and the reaction mixture was stirred for 20 h at room temperature. An additional 6 ml of trifluoroacetic acid was added and the reaction mixture was stirred for an additional 24 h at room temperature. The volatiles were evaporated in vacuo and the remainder was dissolved in 0.1 N hydrochloric acid (100 ml) and stirred for 24 h. The precipitate was filtered off and washed with water (3×20 ml), dried in vacuo at 50° C. and recrystallised from ethyl acetate affording 1.06 g (27%) of the title compound as a solid.

HPLC retention time=20.77 minutes. (water/acetonitrile 8:2, 0.01 N (NH$_4$)$_2$SO$_4$ buffer, pH=2.5) $^1$H NMR (200 MHz, DMSO-d$_6$): $\delta_H$ 2.75–3.90 (m, 8H), 4.55 (bs, 2H), 6.58 (d, 1 H), 6.85 (t, 1 H), 6.99 (d, 2H), 7.27 (t, 2H), 7.48–7.66 (m, 3H), 7.89 (m, 1 H), 8.05 (d, 1 H).

EXAMPLE 3
3-(1-Biphenyl-4-ylmethyl-1H-indol-3-yl)acrylic acid

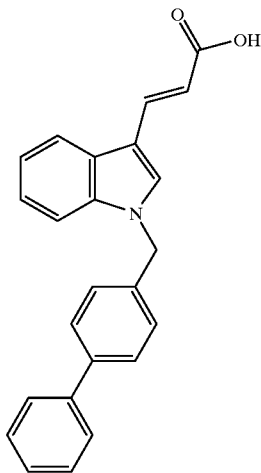

To a solution of 3-(indol-3-yl)acrylic acid ethyl ester (2.2 g, 10 mmol) in N,N-dimethylformamide (40 ml) was added sodium hydride (440 mg, 11 mmol, 60% in mineral oil). After stirring at room temperature for 1 h 4-phenyl-benzylchloride (2.28 g, 11 mmol) and potassium iodide (170 mg, 1 mmol) were added. The resulting reaction mixture was stirred at room temperature for 4 h and poured on to ice water (400 ml). The precipitate was filtered off and washed with water (2×50 ml) and dried in vacuo at 50° C. for 18 h. The crude product was washed with heptane, filtered off and dried in vacuo at 50° C. affording 3.75 g of an solid which was recrystallised from acetonitrile (50 ml) affording 3.25 g (85%) of 3-(1-biphenyl-4-ylmethyl-1H-indol-3-yl)acrylic acid ethyl ester as a solid. To a mixture of the above indol acrylic acid ethyl ester (3.25 g, 8.5 mmol), ethanol (25 ml), water (25 ml), and tetrahydrofuran (25 ml) was added sodium hydroxide (1.03 g, 26 mmol) and the mixture was stirred at 50° C. for 24 h. Water (250 ml) was added and the reaction mixture was extracted with diethyl ether (2×100 ml). pH of the aqueous phase was adjusted to pH=2 with 5N hydrochloric acid and the precipitate was filtered off, washed with water (3×15 ml) and dried in vacuo at 50° C. affording 2.87 g (96%) of the title compound as a solid.

Calculated for C$_{24}$H$_{19}$NO$_2$; C, 81.56 %; H, 5.42 %; N, 3.96%. Found: C, 81.47 %; H, 5.61 %; N, 3.70%.

EXAMPLE 4
3-(1-Biphenyl-4-ylmethyl-1H-imidazol-4-yl)acrylic acid

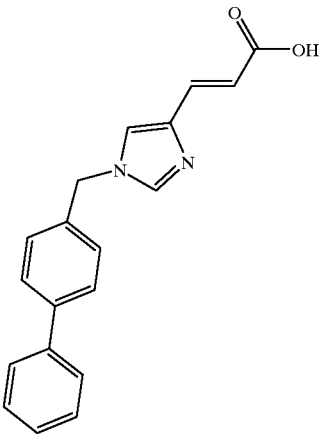

To a solution of urocanic acid (25 g, 0.181 mol) in methanol (300 ml) was slowly added concentrated sulphuric acid (11.2 ml, 0.199 mol) and the reaction mixture was stirred at reflux temperature for 19 h. The reaction mixture was cooled and the volatiles were evaporated in vacuo. The resulting solid was stirred for 1 h with a mixture of diethyl ether and methanol (9:1) (200 ml). The remaining solid was filtered off, washed with acetone (80 ml), diethyl ether (100 ml) and dried in vacuo at 50° C. for 48 h which afforded 46.7 g (100%) of urocanic acid methyl ester dihydrogen sulphate.

To a suspension of potassium carbonate (25.5 g, 184 mmol) in dry N,N-dimethylformamide (200 ml) was added the above methyl ester (11.52 g, 46.05 mmol) and the mixture was stirred for 1 h at room temperature. 4-(Chloromethyl)biphenyl (10.0 g, 48.4 mmol) and potassium iodide (100 mg) was added and the reaction mixture was stirred at 45° C. for 18 h under an atmosphere of dry nitrogen. The cooled reaction mixture was poured into a mixture of ice water (400 ml) and saturated aqueous ammonium chloride (100 ml) and extracted with ethyl acetate (3×200 ml). The combined organic extracts were washed with water (3×150 ml), dried (MgSO$_4$) and evaporated in vacuo-which afforded a solid which was washed with diethyl ether (100 ml) filtered off and air dried. Recrystallisation from isopropanol (50 ml) afforded after drying in vacuo at 50° C. 11.2 g (76%) of 3-(1-biphenyl-4-ylmethyl-1H-imidazol-4-yl)acrylic acid methyl ester as a solid.

To a solution of the above methyl ester (2.0 g, 6.28 mmol) in a mixture of ethanol (10 ml), tetrahydrofuran (15 ml) and water (10 ml) was added sodium hydroxide (377 mg, 9.4 mmol) and the resulting mixture was stirred at room temperature for 22 h. The precipitate was filtered off and washed with a mixture of ethanol and tetrahydrofuran (1:2) followed by diethyl ether and dried in vacuo at 50° C. which afforded 1.29 g (63%) of the title compound as the sodium salt.

Calculated for $C_{19}H_{15}NaN_2O_2$, 1.75 $H_2O$: C, 63.77%; H, 5.21%; N, 7.83%. Found: C, 63.55%; H, 5.21%; N, 7.73.

HPLC retention time=4.16 minutes. (water/acetonitrile 1:1, 0.01 N $(NH_4)_2SO_4$ buffer, pH=2.5)

$^1$H NMR (200 MHz, MeOH-$d_4$): $\delta_H$ 5.14 (s, 2H), 6.39 (d, 1H, $J_H$=15.8 Hz), 7.12–7.35 (m, 7H), 7.49–7.55 (m, 4H), 7.64 (d, 1 H).

EXAMPLE 5

3-(3-(2-(4-Quinolin-2-yl-piperazin-1-yl)ethyl)phenyl) acrylic acid hydrochloride

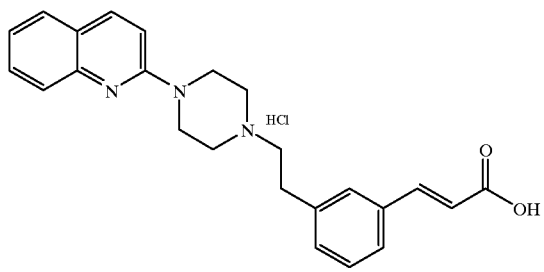

A mixture of 2-chloroquinoline (10.0 g, 60.5 mmol), piperazine (26.1 g, 303 mmol) and pyridine (15 ml) was heated reflux temperature for 4 h. The hot reaction mixture was poured into a conical flask and diluted with tetrahydrofuran (150 ml). The precipitated solid was filtered off and washed with diethyl ether (3×50 ml) and the combined organic phases were evaporated in vacuo. The residue was suspended in a mixture of diethyl ether (200 ml) and 96% ethanol (80 ml) and undissolved solid was filtered off and washed with diethyl ether. The organic phase was evaporated in vacuo affording a solid which was crushed under water (200 ml) filtered off and washed with water (3×50 ml), diethyl ether (3×40 ml), dried in vacuo at 50° C. affording 11.8 g (92%) of 2-(1-piperazinyl)quinoline as a solid.

A mixture of the above quinoline (7.0 g, 32.8 mmol), 2-bromo-1-(3-bromophenyl)ethanone (9.12 g, 32.82 mmol), potassium carbonate (13.61 g, 98.46 mmol) and methyl ethyl ketone (150 ml) was heated at 80° C. for 18 h. The cooled reaction mixture was poured into water (250 ml) and extracted with ethyl acetate (150 ml). The organic phase was washed with 10% aqueous sodium chloride (3×150 ml), dried ($MgSO_4$), filtered and evaporated in vacuo affording a syrup which was crystallised from a mixture of heptane (200 ml) and diethyl ether (50 ml) affording, after drying in vacuo at 50° C., 10.8 g (80%) of 1-(3-bromophenyl)-2-(4-quinolin-2-yl-piperazin-1-yl)ethanone as a solid.

To a mixture of the above ethanone (4.0 g, 9.75 mmol), potassium hydroxide (1.86 g, 33.15 mmol, powder) and diethyleneglycol (60 ml) under an atmosphere of nitrogen was added hydraizine hydrate (1.2 ml, 22.4 mmol). The resulting reaction mixture was heated at 110° C. for 2 h with a condenser attached to the reaction flask followed by 1 h without condenser. The temperature was raised to 140° C. for 1 h and finally to 190° C. for 15 min. The resulting reaction mixture was allowed to cool to room temperature and stirred at this temperature for 18 h. Water (20 ml) was added and the precipitate was filtered off, washed with water (4×100 ml), heptane (3×15 ml) and dried in vacuo at 50° C. which afforded 2.22 g (58%) of 2-(4-(2-(3-bromophenyl)ethyl)piperazin-1-yl)quinoline as a solid.

A mixture of the above piperazine (2.0 g, 5.05 mmol), tert-butyl acrylate (1.05 ml, 6.56 mmol), palladium acetate (12 mg, 0.051 mmol), tri-ortho-tolyl phosphine (62 mg, 0.202 mmol) in triethylamine (10 ml) under an atmosphere of nitrogen was stirred at 100° C. for 24 h in an screw cap ampoule. The cooled reaction mixture was diluted with ethyl acetate (50 ml) and the solid filtered off and washed ethyl acetate (25 ml). The combined organic phases were washed with water (3×80 ml), dried ($MgSO_4$), filtered and evaporated in vacuo. The residue was purified by column chromatography on silicagel (400 ml) using a mixture of ethyl acetate and heptane (1:1) as eluent affording a syrup which was crystallised from heptane (20 ml). The solid was filtered off and washed with heptane, dried in vacuo at 50° C. affording 1.51 g (67%) of 3-(3-(2-(4-quinolin-2-yl-piperazin-1-yl)ethyl)phenyl)acrylic acid tert-butyl ester as a solid.

To a mixture of the above tert-butyl ester (1.0 g, 2.25 mmol) in dichloromethane (10 ml) was added trifluoroacetic acid (2.5 ml) and the mixture was stirred for 18 h at room temperature. The reaction mixture was evaporated in vacuo, the residue was dissolved in isopropanol (20 ml) and evaporated in vacuo (repeated two times). The remaining syrup was dissolved in diethyl acetate (50 ml). 1N sodium hydroxide was added until pH=8 and the precipitate was filtered off washed with water, diethyl ether and ethyl acetate, dried in vacuo at 50° C. affording 790 mg (93%) of the title compound as the free acid. To 500 mg of the free acid dissolved in tetrahydrofuran (10 ml) was added 1N hydrochloric acid (20 ml) and the resulting mixture was stirred at room temperature for 18 h. The precipitate was filtered off, washed with tetrahydrofuran (10 ml), isopropanol (10 ml) and diethyl ether (10 ml), dried in vacuo at 50° C. for 18 h affording 350 mg (63 %) of the title compound as a solid.

Calculated for $C_{24}H_{25}N_3O_2$, 1HCl, 3$H_2O$: C, 60.31%; H, 6.75%; N, 8.79. Found: C, 60.09%; H, 6.64%; N, 8.63.

HPLC retention time 4.27 minutes. (water/acetonitrile 7:3, 0.01 N $(NH_4)_2SO_4$ buffer, pH=2.5).

EXAMPLE 6

3-(5-Oxo-10,11-dihydro-5H-dibenzo[a,d]cyclohepten-2-yl) acrylic acid

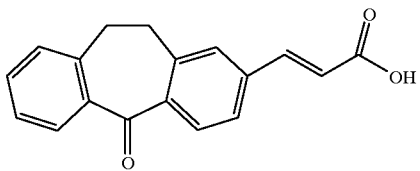

A mixture of phthalic acid anhydride (43 g, 0.291 mol), 3-bromophenyl acetic acid (62.5 g, 0.291 mol) and sodium acetate (2 g, 0.015 mol) was heated at 220° C. for 2 h under an atmosphere of nitrogen. The reaction mixture was cooled to about 80° C. and ethanol (75 ml) was added. The precipitate was filtered off, washed with a mixture of heptane and ethanol (9:1) and dried in vacuo at 50° C. which afforded 71 g (81%) of 3-(3-bromobenzylidene)-3H-isobenzofuran-1-one as a solid.

A mixture of the above isobenzofuran (71 g, 0.236 mol), red phosphorus (29.2, 0.943 mol) and 57% aqueous hydrogen iodide (400 ml) was heated at reflux for 18 h. The cooled reaction mixture was poured onto ice water (1.5 l) and pH was made alkaline with 50% aqueous sodium hydroxide. The resulting mixture was extracted with diethyl ether (2×250 ml). pH of the aqueous phase was adjusted to pH=1 with concentrated hydrochloric acid. The precipitate was filtered off, washed with water and heptane, dried in vacuo at 50° C. which afforded 46.6 g (65%) of 2-(2-(3-bromophenyl)ethyl)benzoic acid as a solid.

To a solution of aluminium chloride (48.9 g, 0.366 mol) in dichloro-methane (250 ml) was added dropwise a solution of 2-(2-(3-bromophenyl)ethyl)benzoyl chloride (50 g, 0.153 mol) in dichloromethane (200 ml) at room temperature. The reaction mixture was stirred for 2 h at room temperature and poured onto ice water (750 ml). The organic phase was separated, dried (MgSO$_4$), filtered and evaporated in vacuo which afforded 43.3 g (99%) of 2-bromo-10,11-dihydro-5H-dibenzo[a,d]cycloheptan-5-one as a solid.

A mixture of 2-bromo-10,11-dihydro-5H-dibenzo[a,d]cycloheptan-5-one (2.0 g, 6.96 mmol), tert-butyl acrylate (1.2 g, 9.05 mmol), palladium acetate (16 mg, 0.07 mmol), tri-o-tolylphosphine (85 mg, 0.290 mmol), triethylamine (10 ml) in N,N-dimethylformamide (50 ml) was heated at 100° C. for 18 h under an atmosphere of nitrogen. The cooled reaction mixture was diluted with water (100 ml), extracted with diethyl ether (2×100 ml). The combined organic extracts were washed with saturated aqueous ammonium chloride (2×100 ml), dried (MgSO$_4$), filtered and evaporated in vacuo. The residue (1.8 g) was purified by column chromatography on silicagel (600 ml) using a mixture of ethyl acetate and heptane (1:10) as eluent affording 0.7 g (30%) of 3-(5-oxo-10,11-dihydro-5H-dibenzo[a,d]cyclohepten-2-yl)acrylic acid tert-butyl ester as an oil.

To a mixture of the above tert-butyl ester (0.7 g, 2.09 mmol) in dichloromethane (40 ml) was added trifluoroacetic acid (2.5 ml) and the mixture was stirred for 18 h at room temperature. An additional 0.5 ml of trifluoroacetic acid was added and the reaction mixture was stirred for an additional 18 h at room temperature. The reaction mixture was washed with water (50 ml), dried (MgSO$_4$), filtered and evaporated in vacuo affording an solid which was dried in vacuo at 50° C. for 18 h. This afforded 0.12 g (21%) of the title compound as a solid.

Calculated for C$_{18}$H$_{14}$O$_3$: C, 76.94%; H, 5.13%. Found: C, 76.89%; H, 5.08%.

m.p.: 234–236° C. HPLC retention time=10.0 minutes. (water/acetonitrile 1:1, 0.01 N (NH$_4$)$_2$SO$_4$ buffer, pH=2.5).

EXAMPLE 7
3-(2,3-Dihydro-benzo[b]furan-5-yl)acrylic acid

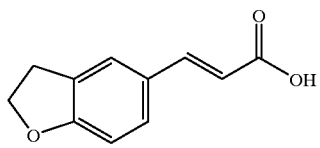

A mixture of 5-bromo-2,3-dihydro-benzo[b]furan (9.95 g, 0.05 mol), tert-butyl acrylate (9.71 g, 0.075 mol), palladium tetrakistriphenylphosphine (200 mg, 0.2 mmol), triethylamine (11 ml) in N,N-dimethylformamide (40 ml) was heated at reflux temperature for 20 h under an atmosphere of nitrogen. The cooled reaction mixture was diluted with water (150 ml) and extracted with ethyl acetate (2×50 ml). The combined organic extracts were washed with water (50 ml), saturated aqueous ammonium chloride (20 ml), dried (MgSO$_4$), filtered and evaporated in vacuo. The residue was recrystallised from heptane affording after drying 1.55 g 13%) of 3-(2,3-dihydro-benzo[b]furan-5-yl)acrylic acid tert butyl ester as a solid.

To a solution of the above tert butyl ester (1.23 g, 5 mmol) in dichloromethane (10 ml) was added trifluoroacetic acid (2.5 ml) and the reaction mixture was stirred at room temperature for 20 h. The volatiles were evaporated in vacuo, the residue was dissolved in toluene (20 ml) and evaporated in vacuo (repeated three times) affording a crude product. The crude product was purified by column chromatography on silicagel (180 ml) using a mixture of ethyl acetate, heptane and formic acid (45:45:10) as eluent. This afforded 0.37 g which was recrystallised from ethyl acetate affording 0.16 g (16%) of the title compound as a solid.

Calculated for C$_{11}$H$_{10}$O$_3$: C, 69.46%; H, 5.30%. Found: C, 69.32%; H, 5.45%.

HPLC retention time=4.4 minutes. (water/acetonitrile 1:1, 0.01 N (NH$_4$)$_2$SO$_4$ buffer, pH=2.5).

EXAMPLE 8
3-(9-Biphenyl-4-ylmethyl-9H-carbazol-3-yl)acrylic acid

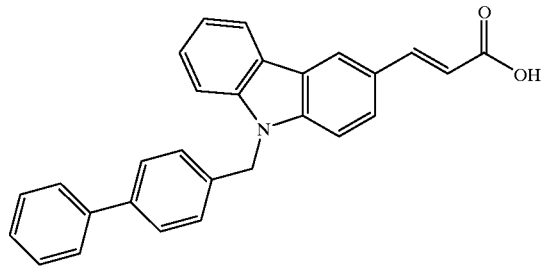

To a solution of 3-bromo-9H-carbazole (7.38 g, 30 mmol, prepared as described in Tetrahedron (1992), 48, 4779) in N,N-dimethylformamide (200 ml) was added portion wise sodium hydride (1.6 g, 39 mmol, 60% in mineral oil) during 15 min. After stirring at room temperature for 1 h, 4-phenylbenzylchloride (6.21 g, 30 mmol) was added portion wise during 10 min. The resulting reaction mixture was stirred at room temperature for 20 h poured onto water (300 ml) and stirred for 4 h. The precipitate was filtered off, washed with water (3×150 ml) and dried in vacuo at 50° C. for 18 h. The crude product was washed with heptane, filtered off and dried in vacuo at 50° C. affording 12 g (100%) of 9-(biphenyl-4-ylmethyl)-3-bromo-9H-carbazole as a solid.

A mixture of the above bromo-carbazole (7.15 g, 18 mmol), tert-butyl acrylate (3.01 g, 23.3 mmol), palladium acetate (40 mg, 0.2 mmol), tri-o-tolylphosphine (220 mg, 0.7 mmol) and triethylamine (10 ml) in an screw cap ampoule was heated at 100° C. for 20 h. The cooled reaction mixture was diluted with ethyl acetate (75 ml), washed with water (3×20 ml), dried (MgSO$_4$), filtered and evaporated in vacuo. The residue (9.6 g) was purified by column chromatography on silicagel (600 ml) using toluene as eluent which afforded 4.92 g (60%) of 3-(9-(biphenyl-4-ylmethyl)-9H-carbazol-3-yl)acrylic acid tert-butyl ester as a solid.

To a solution of the above tert-butyl ester (1.38 g, 3 mmol) in dioxane (15 ml) was added lithium hydroxide hydrate (640 mg, 15 mmol) and water (15 ml) the reaction mixture was stirred at reflux temperature for 24 h. The cooled reaction mixture was diluted with water (50 ml) and acidified with 5N hydrochloric acid to pH=1. The precipitate was filtered off and washed with water (3×15 ml), diethyl ether (3×15 ml) and dried in vacuo. The crude product was suspended in a mixture of diethyl ether (30 ml) and tetrahydrofuran (15 ml) and stirred at room temperature for 68 h. The precipitate was filtered off and washed with diethyl ether and dried in vacuo affording 0.89 g (74%) of the title compound as a solid.

Calculated for $C_{28}H_{21}NO_2$: C, 83.35%; H, 5.25%; N, 3.47%. Found: C, 83.24%; H, 5.25%; N, 3.24%.

m.p.: 257–257.5° C. HPLC retention time=11.7 minutes. (water/acetonitrile 3:7, 0.01 N $(NH_4)_2SO_4$ buffer, pH=2.5).

EXAMPLE 9

3-(10,11-Dihydro-5H-dibenzo[b,f]azepin-2-yl)acrylic acid

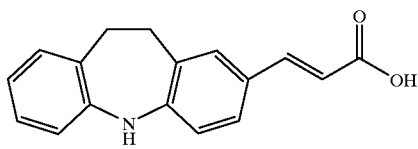

A mixture of 2-bromo-10,11-Dihydro-5H-dibenzo[b,f] azepin (4.11 g, 15 mmol, prepared as described in Tetrahedron (1992), 48, 4779) tert-butyl acrylate (2.91 g, 22.5 mmol), palladium acetate (40 mg, 0.2 mmol), tri-o-tolylphosphine (183 mg, 0.6 mmol) and triethylamine (20 ml) in an screw cap ampoule was heated at 100° C. for 20 h. The cooled reaction mixture was diluted with ethyl acetate (50 ml), washed with water (3×20 ml), dried ($MgSO_4$), filtered and evaporated in vacuo. The residue (3.9 g) was purified by column chromatography on silicagel (600 ml) using a mixture of ethyl acetate and heptane (1:6) as eluent which afforded 1.62 g (34%) of 3-(10,11-dihydro-5H-dibenzo[b,f]azepin-2-yl)acrylic acid tert-butyl ester as a solid.

To a solution of the above tert-butyl ester (600 mg, 1.9 mmol) in dioxane (15 ml) was added lithium hydroxide hydrate (400 mg, 9.3 mmol) and water (15 ml) the reaction mixture was stirred at reflux temperature for 16 h. The cooled reaction mixture was decanted and diluted with water (60 ml). Acidified with 5N hydrochloric acid to pH=1. The precipitate was filtered off, washed with water (3×15 ml) and dried in vacuo affording 409 mg (82%) of the title compound as a solid.

Calculated for $C_{17}H_{14}NO_2$: C, 77.25%; H, 5.34%; N, 5.30%. Found: C, 76.98%; H, 5.86%; N, 5.09%.

m.p.: 215–216° C.

$^1$H NMR (200 MHz, DMSO-$d_6$): $\delta_H$ 2.98 (s, 4H), 6.28 (d, 1H, $J_H$=15.7 Hz), 6.74 (dt, 1H), 7.04 (m, 4H), 7.38 (m, 2H), 7.46 (d, 1H, $J_H$=15.7), 8.74 (1 H, S, NH), 12.05 (bs, 1 H).

HPLC retention time=10.76 minutes. (water/acetonitrile 1:1, 0.01 N $(NH_4)_2SO_4$ buffer, pH=2.5)

EXAMPLE 10

The PTP1B and PTPα cDNA was obtained by standard polymerase chain reaction technique using the Gene Amp Kit according to the manufacturers instructions (Perkin Elmer/Cetus). The oligonucleotide primers were designed according to published sequences (Chernoff et al., *Proc. Natl. Acad. Sci. U.S.A.* 87: 2735–2739 (1990); Krueger et al., *EMBO J.* 9: 3241–3252 (1990)) including convenient restriction nuclease sites to allow cloning into expression vectors. The cDNA corresponding to the full-length sequence of PTP1B and the intracellular part of PTPα were introduced into the insect cell expression vector pVL1392.

The proteins were expressed according to standard procedures. PTP1B was semi-purified by ion exchange chromatography, and PTPα was purified to apparent homogeneity using a combination of ion exchange chromatography and gel filtration techniques using standard procedures. TC-PTP and LAR domain 1 were obtained from New England Biolabs. Yersinia PTP was a kind gift from J. E. Dixon, The University of Michigan, Ann Arbor, U.S.A. p-Nitrophenyl phosphate was purchased from Sigma and used without further purification.

Methods p-Nitrophenyl phosphate (pNPP) is a general phosphatase substrate including a substrate for PTPases. When pNPP (colorless) is hydrolyzed by a phosphatase to phosphate and p-nitrophenolate (yellow in alkaline solutions) the enzyme reaction can be followed by measuring the optical density at 410 nm after adjusting the pH appropriately. pNPP was used as general substrate to analyze the PTPase inhibitory capacity of the compounds of the invention.

The inhibiting effect of a compound is given by its $K_i$ value, which expresses the concentration of inhibitor ($\mu$M) in the reaction mixture necessary for a 50 percent reduction of the enzyme activity.

The $K_i$ may be determined by a titration curve using several appropriately diluted solutions of the inhibitor or by using the following more simple formula, when the concentration of inhibitor is in large excess of the enzyme concentration:

$$K_i = I_o \times E / (E_o - E)$$

where $I_o$ is the concentration of inhibitor ($\mu$M) added to the reaction mixture, E is the activity of the enzyme in the reaction mixture containing the inhibitor, and $E_o$ is the enzyme activity in a corresponding control reaction mixture without the inhibitor.

The $K_i$ values of inhibitors towards PTP1B were measured as follows. In all cases the inhibiting effects were determined at pH 5.5 and at 37° C. with a reaction time of 60 minutes.

The reaction mixtures were:

1) 25 µl enzyme solution 25 µl inhibitor solution in DMSO 500 µl substrate solution or 2) 25 µl enzyme solution 25 µl DMSO 500 µl substrate solution The substrate solution contained 0.2 M acetate buffer, pH 5.5, 11 mM p-nitrophenyl phosphate, 5.5 mM dithiotreitol.

The reaction was stopped by addition of 4 ml 0.2 N NaOH, and the enzyme activity was determined by measuring the release of p-nitrophenol at 410 nm. The inhibiting effect was calculated as shown above.

The $K_i$ values of inhibitors towards TC-PTP, LAR domain1, PTPα domain 1+2, and Yersinia PTP were measured essentially as described for PTP1B with the exception that all reactions were carried out in 96-wells microtiter plates. In all cases the inhibiting effects were determined at pH 5.5 and at room temperature with a reaction time of 15 minutes.

The reaction mixtures were:

1) 5 µl enzyme solution 5 µl inhibitor solution in DMSO (final concentration 100 µM) 90 µl substrate solution or 2) 5 μl enzyme solution 5 μl DMSO 90 μl substrate solution The final concentrations: 0.2 M acetate buffer, pH 5.5, 5 mM p-nitrophenyl phosphate, 5 mM dithiotreitol.

The reaction was stopped by addition of 100 μl 0.4 N NaOH, and the enzyme activity was determined by measuring the release of p-nitrophenol at 405 nm. The inhibiting effect was calculated as shown above.

Results

Using the above assay systems we have demonstrated that compounds of the invention are PTPase inhibitors.

We claim:

1. A compound of formula (I):

L—Ar₁—CH=CH—COOR₁     (I)

wherein
Ar₁ is phenyl; and
L is A—Y₁—W₁—X—W₂—Y₂— wherein W₁ and W₂ are independently a chemical bond or saturated or unsaturated $C_{1-6}$-alkylene; X is a chemical bond, CO, CONR₇, NR₇CO, NR₇, O, S, SO, or SO₂; Y₁ and Y₂ are independently a chemical bond, O, S, or NR₇; wherein R₇ is hydrogen, $C_{1-6}$-alkyl or COZ₂ wherein Z₂ is $C_{1-6}$-alkyl; and A is biphenyl, phenyl-piperazinyl, or quinolinyl-piperazinyl; and
R₁ is hydrogen or $C_{1-6}$-alkyl;
or a pharmaceutically acceptable salt thereof.

2. The compound of claim 1 wherein the cinnamic double bond conformation is trans (E).

3. The compound of claim 1 wherein W₁ and W₂ are independently a chemical bond or saturated $C_{1-6}$-alkylene, X is a chemical bond and Y₁ and Y₂ are independently a chemical bond or O.

4. The compound of claim 1 wherein A is biphenyl.

5. The compound of claim 4 wherein A is 3-biphenyl-4-yl.

6. The compound of claim 1 wherein A is phenyl-piperazinyl.

7. The compound of claim 6 wherein A is 4-phenyl-piperazin-1-yl.

8. The compound of claim 1 wherein A is quinolinyl-piperazinyl.

9. The compound of claim 8 wherein A is 4-quinolin-2-yl-piperazin-1-yl.

10. The compound of claim 1 which is:
3-(3-Biphenyl-4-yloxymethyl)phenyl)acrylic acid,
3-(2-(4-Phenyl-piperazin-1-ylmethyl)phenyl)acrylic acid,
3-(3-(2-(4-Quinolin-2-yl-piperazin-1-yl)ethyl)phenyl) acrylic acid, or
a pharmaceutically acceptable salt thereof.

11. An immobilized compound comprising a suitable solid-phase coupled with a compound of claim 1.

12. A pharmaceutical composition comprising the compound of claim 1 together with a pharmaceutically acceptable carrier or diluent.

13. A compound of formula (II):

L$_n$—Ar₁—CH=CH—COOR₁     (II)

wherein
Ar₁ is indolyl, imidazolyl or 9H-carbazolyl; and
n is 1, 2, 3, 4 or 5;
L is independently hydrogen, $C_{1-6}$-alkyl, $C_{1-6}$-alkoxy, hydroxy, halogen, trihalogenomethyl, hydroxy-$C_{1-6}$-alkyl, amino-$C_{1-6}$-alkyl, COR₂, NO₂, CN, CHO, $C_{1-6}$-alkanoyloxy, carbamoyl, or NR₅R₆, wherein R₂ is $C_{1-6}$-alkyl, OH, or NR₃R₄ wherein R₃ and R₄ independently are hydrogen or $C_{1-6}$-alkyl; and R₅ and R₆ independently are hydrogen, $C_{1-6}$-alkyl, or COZ₁ wherein Z₁ is $C_{1-6}$-alkyl; or L is A—Y₁—W₁—X—W₂—Y₂— wherein W₁ and W₂ are independently a chemical bond or saturated or unsaturated $C_{1-6}$-alkylene; X is a chemical bond, CO, CONR₇, NR₇CO, NR₇, O, S, SO, or SO₂; Y₁ and Y₂ independently are a chemical bond, O, S, or NR₇; wherein R₇ is hydrogen, $C_{1-6}$-alkyl and Z₂ is $C_{1-6}$-alkyl; and A is biphenyl; and
R₁ is hydrogen or $C_{1-6}$-alkyl;
or a pharmaceutically acceptable salt thereof.

14. The compound of claim 13 wherein the cinnamic double bond conformation is trans (E).

15. The compound of claim 13 wherein W₁ is a saturated $C_{1-6}$allylene and Y₁, X, W₂ and Y₂ are each a chemical bond.

16. The compound of claim 13 wherein n is 1.

17. The compound of claim 13 wherein Ar₁ is 1H-indolyl-3-yl.

18. The compound of claim 13 wherein Ar₁ is imidazol-4-yl.

19. The compound of claim 13 wherein Ar₁ is 9H-carbazol-3-yl.

20. A compound of claim 13 which is:
3-(1-Biphenyl-4-ylmethyl-1H-indol-3-yl)acrylic acid,
3-(1-Biphenyl-4-ylmethyl-1H-imidazol-4-yl)acrylic acid,
3-(9-Biphenyl-4-ylmethyl-9H-carbazol-3-yl)acrylic acid, or
a pharmaceutically acceptable salt thereof.

21. An immobilized compound comprising a suitable solid-phase coupled with the compound of claim 13.

22. A pharmaceutical composition comprising the compound of claim 13 together with a pharmaceutically acceptable carrier or diluent.

23. A compound of formula (III):

L$_n$—Ar₁—CH=CH—COOR₁     (III)

wherein
Ar₁ is 5-Oxo-10,11-dihydro-5H-dibenzo[a,d]cycloheptenyl, 2,3-Dihydrobenzo[b]furanyl or 10,11-Dihydro-5H-dibenzo[b,f]azepinyl;
n is 1, 2, 3, 4 or 5;
L is independently hydrogen, $C_{1-6}$-alkyl, $C_{1-6}$-alkoxy, hydroxy, halogen, trihalogenomethyl, hydroxy-$C_{1-6}$-alkyl, amino-$C_{1-6}$-alkyl, COR₂, NO₂, CN, CHO, $C_{1-6}$-alkanoyloxy, carbamoyl, or N₅R₆, wherein R₂ is $C_{1-6}$-alkyl, OH, or NR₃R₄ wherein R₃ and R₄ independently are hydrogen and $C_{1-6}$-alkyl; and R₅ and R₆ independently are hydrogen, $C_{1-6}$-alkyl, or COZ₁ wherein Z₁ is $C_{1-6}$-alkyl; or L is A—Y₁—W₁—X—W₂—Y₂— wherein W₁ and W₂ are independently a chemical bond or saturated or unsaturated $C_{1-6}$-alkylene; X is a chemical bond, CO, CONR₇, NR₇CO, NR₇, O, S, SO, or SO₂; Y₁ and Y₂ independently are a chemical bond, O, S, or NR₇; wherein R₇ is hydrogen, $C_{1-6}$-alkyl and Z₂ is $C_{1-6}$-alkyl; and A is biphenyl; and
R₁ is hydrogen or $C_{1-6}$-alkyl;
or a pharmaceutically acceptable salt thereof.

24. The compound of claim 23 wherein the cinnamic double bond conformation is trans (E).

25. The compound of claim 23 wherein n is 1.

26. The compound of claim 23 wherein L is hydrogen.

27. The compound of claim 23 wherein Ar₁ is 5-Oxo-10,11-dihydro-5H-dibenzo[a,d]cyclohepten-2-yl.

28. The compound of claim 23 wherein Ar₁ is 2,3-dihydrobenzo[b]furan-5-yl.

29. The compound of claim 23 wherein Ar₁ is 10,11-Dihydro-5H-dibenzo[b,f]azepin-2-yl.

30. The compound of claim 23 which is:
3-(5-Oxo-10,11-dihydro-5H-dibenzo[a,d]cyclohepten-2-yl)acrylic acid,
3-(2,3-Dihydro-benzo[b]furan-5-yl)acrylic acid, 3-(10,11-Dihydro-5H-dibenzo[b,f]azepin-2-yl)acrylic acid, or
a pharmaceutically acceptable salt thereof.

31. An immobilized compound comprising a suitable solid-phase coupled with the compound of claim 23.

32. A pharmaceutical composition comprising the compound of claim 23 together with a pharmaceutically acceptable carrier or diluent.

33. A method of treating or preventing type I diabetes, type II diabetes, impaired glucose tolerance, insulin resistance, obesity, immune dysfunctions, diseases with dysfunctions of the coagulation system, allergic diseases, osteoporosis, proliferative disorders, diseases with decreased or increased synthesis or effects of growth hormone, diseases with decreased or increased synthesis of hormones or cytokines that regulate the release of/or response to growth hormone, diseases of the brain, and infectious diseases, comprising administering to a subject in need thereof an effective amount of the compound of claim 1.

34. A method of treating or preventing type I diabetes, type II diabetes, impaired glucose tolerance, insulin resistance, obesity, immune dysfunctions, diseases with dysfunctions of the coagulation system, allergic diseases, osteoporosis, proliferative disorders, diseases with decreased or increased synthesis or effects of growth hormone, diseases with decreased or increased synthesis of hormones or cytokines that regulate the release of/or response to growth hormone, diseases of the brain, and infectious diseases, comprising administering to a subject in need thereof an effective amount of the compound of claim 13.

35. A method of treating or preventing type I diabetes, type II diabetes, impaired glucose tolerance, insulin resistance, obesity, immune dysfunctions, diseases with dysfunctions of the coagulation system, allergic diseases, osteoporosis, proliferative disorders, diseases with decreased or increased synthesis or effects of growth hormone, diseases with decreased or increased synthesis of hormones or cytokines that regulate the release of/or response to growth hormone, diseases of the brain, and infectious diseases, comprising administering to a subject in need thereof an effective amount of the compound of claim 23.

* * * * *